US010352867B2

(12) United States Patent
Umemura et al.

(10) Patent No.: US 10,352,867 B2
(45) Date of Patent: Jul. 16, 2019

(54) SURFACE PROPERTY INDEXING APPARATUS, SURFACE PROPERTY INDEXING METHOD, AND PROGRAM

(71) Applicant: NIPPON STEEL & SUMITOMO METAL CORPORATION, Tokyo (JP)

(72) Inventors: Jun Umemura, Tokyo (JP); Toshio Akagi, Tokyo (JP)

(73) Assignee: NIPPON STEEL CORPORATION, Tokyo (JP)

( * ) Notice: Subject to any disclaimer, the term of this patent is extended or adjusted under 35 U.S.C. 154(b) by 0 days.

(21) Appl. No.: 15/123,856

(22) PCT Filed: Feb. 19, 2015

(86) PCT No.: PCT/JP2015/054584
§ 371 (c)(1),
(2) Date: Sep. 6, 2016

(87) PCT Pub. No.: WO2015/133287
PCT Pub. Date: Sep. 11, 2015

(65) Prior Publication Data
US 2017/0016832 A1    Jan. 19, 2017

(30) Foreign Application Priority Data

Mar. 7, 2014  (JP) ................................ 2014-044899

(51) Int. Cl.
G01N 21/86       (2006.01)
G01N 21/892      (2006.01)
(Continued)

(52) U.S. Cl.
CPC ............. G01N 21/86 (2013.01); G01B 11/24 (2013.01); G01J 3/504 (2013.01); G01N 21/251 (2013.01);
(Continued)

(58) Field of Classification Search
USPC ........................................................ 348/86
See application file for complete search history.

(56) References Cited

U.S. PATENT DOCUMENTS

2003/0193669 A1* 10/2003 Takagi ..................... G01J 3/46
356/446
2004/0246493 A1* 12/2004 Kim ................... G01B 11/0625
356/504
(Continued)

FOREIGN PATENT DOCUMENTS

CN    101504277 A    8/2009
CN    102365522 A    2/2012
(Continued)

OTHER PUBLICATIONS

Extended European Search Report for European Application No. 15758411.1, dated Sep. 28, 2017.
(Continued)

Primary Examiner — Behrooz M Senfi
Assistant Examiner — Ana Picon-Feliciano
(74) Attorney, Agent, or Firm — Birch, Stewart, Kolasch & Birch, LLP

(57) ABSTRACT

A surface property indexing apparatus includes a measurement device that generates a plurality of captured images and an arithmetic processing apparatus that indexes a surface property of the measured object. The captured images are of the same wavelength of the reflected light that forms images in an image capturing device, and is of different reflection angles of the reflected light that forms images in the image capturing device in the direction corresponding to the longitudinal direction of the measured object in the captured image. The arithmetic processing apparatus reconstructs the generated captured images to generate processing target images having a common wavelength of the reflected light and a common reflection angle of the reflected light and
(Continued)

composed of pixels corresponding to the different view field positions of the measured object, and indexes the surface property of the measured object on the basis of the generated processing target images.

24 Claims, 14 Drawing Sheets

(51) Int. Cl.
    *G01N 21/89* (2006.01)
    *G01B 11/24* (2006.01)
    *G01N 21/25* (2006.01)
    *G06T 7/00* (2017.01)
    *G01J 3/50* (2006.01)
    *G01N 33/20* (2019.01)
    *G01N 21/84* (2006.01)

(52) U.S. Cl.
    CPC ......... *G01N 21/255* (2013.01); *G01N 21/892* (2013.01); *G01N 21/8914* (2013.01); *G06T 7/0004* (2013.01); *G01N 33/20* (2013.01); *G01N 2021/8455* (2013.01); *G01N 2201/062* (2013.01); *G01N 2201/12* (2013.01); *G06T 2207/10004* (2013.01); *G06T 2207/10024* (2013.01); *G06T 2207/30136* (2013.01)

(56) References Cited

U.S. PATENT DOCUMENTS

| 2012/0019836 A1 | 1/2012 | Honma et al. | |
| 2013/0128026 A1* | 5/2013 | Hirose | G01N 21/8903 348/125 |
| 2015/0131090 A1* | 5/2015 | Osumi | G01J 3/504 356/300 |

FOREIGN PATENT DOCUMENTS

| CN | 102630299 A | 8/2012 | | |
| EP | 1353156 A2 | 10/2003 | | |
| EP | 2495552 A1 | 9/2012 | | |
| EP | 2813829 A1 | 12/2014 | | |
| JP | 63-218847 A | 9/1988 | | |
| JP | 2005-62968 A | 3/2005 | | |
| JP | 2009-42978 A | 2/2009 | | |
| JP | 2009-118359 A | 5/2009 | | |
| JP | 2009-162714 A | 7/2009 | | |
| JP | WO 2013157641 A1 * | 10/2013 | .............. | G01J 3/504 |
| KR | 10-2011-0061643 A | 6/2011 | | |
| WO | WO 92/00517 A1 | 1/1992 | | |
| WO | WO 9200517 A1 * | 1/1992 | ......... | G01N 21/8903 |
| WO | WO 2013/118868 A1 | 8/2013 | | |
| WO | WO 2013/157641 A1 | 10/2013 | | |

OTHER PUBLICATIONS

International Search Report, issued in PCT/JP2015/054584, dated May 19, 2015.

Written Opinion of the International Searching Authority, issued in PCT/JP2015/054584 (PCT/ISA/237), dated May 19, 2015.

Chinese Office Action and Search Report for corresponding Chinese Application No. 201580012628.6, dated May 4, 2018, with an English Translation of the Office Action.

Chinese Office Action for corresponding Chinese Application No. 201580012628.6, dated Sep. 25, 2018, with partial English translation.

* cited by examiner

FIG. 6
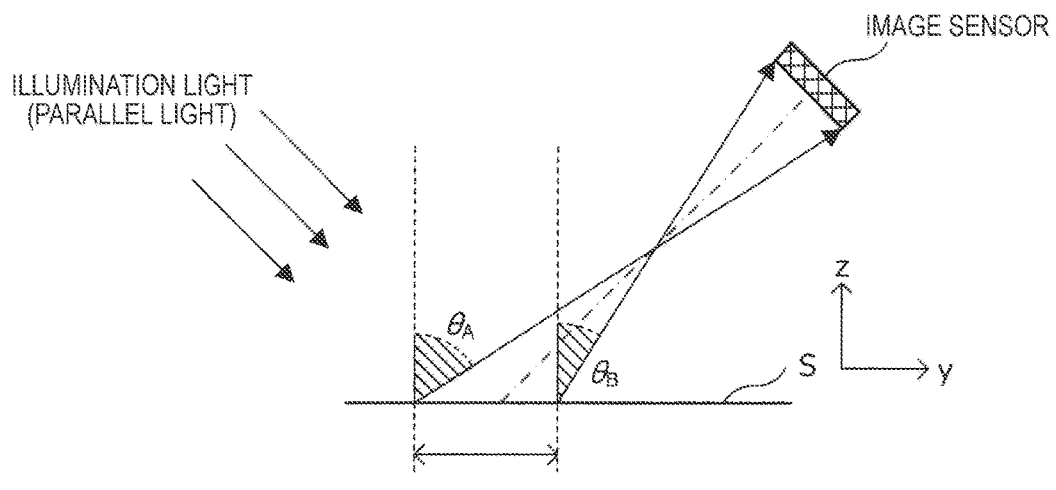
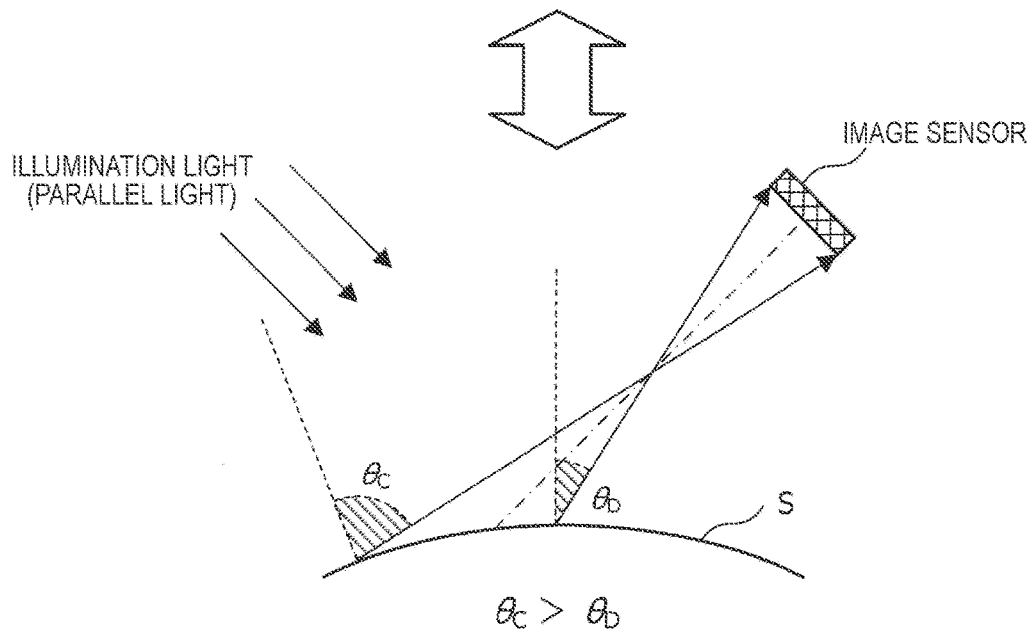

RECONSTRUCTED PROCESSING TARGET IMAGE

BRIGHTNESS VALUE OF PIXEL P
$I(x, y, \lambda_1, \cdots, \lambda_N, \theta_1, \cdots, \theta_M)$

SURFACE PROPERTY INDEXING APPARATUS, SURFACE PROPERTY INDEXING METHOD, AND PROGRAM

TECHNICAL FIELD

The present invention relates to a surface property indexing apparatus, a surface property indexing method, and a program.

BACKGROUND ART

For example, in order to measure color tone and brightness of a measured object surface such as a steel plate surface, it is general that an image of the surface is captured by utilizing a color camera, to check color hue, saturation, and brightness of the obtained image (RGB, CIE L*a*b*, etc.). However, for example, when a measured object is a steel plate whose color tone and brightness slightly change as the illumination and observation angles change, such as titanium and a part of stainless steel plates, it is unable to observe their change by using a certain constant illumination angle and observation angle. Also, when the measured object is a metal surface, the metal surface has a large contrast between specular reflection and diffuse reflection, and thus a standard RGB camera generates an error in color information, and it is difficult to observe subtle color shade.

From the above reason, a spectral reflectance is measured while changing the wavelength of the illumination light that forms an image in the camera as in Patent Literature 1 below, and the spectral reflectance is measured by utilizing a spectrophotometric colorimeter while changing the angle of the illumination and the camera, in order to accurately measure the color tone and the brightness of the measured object surface.

CITATION LIST

Patent Literature

Patent Literature 1: JP 2009-118359A

SUMMARY OF INVENTION

Technical Problem

However, the technology described in above Patent Literature 1 does not mention performing the measurement while changing the angle of the illumination, and is unable to be employed to measure subtle changes of the color tone and the brightness which are generated on the above titanium, part of stainless steel plates, and the like.

Also, a general spectrophotometric colorimeter contacts a minute region of a diameter of approximately 10 mm for the purpose of measuring the region, and thus the measurement area is narrow and the measurement location is discrete, and it is practically impossible to arrange a plurality of spectrophotometric colorimeters in line and measure every detail of the entire surface of a large measured object such as a steel plate for example. Also, the general spectrophotometric colorimeter measures at three angles or so, and is unable to perform measurement of subtler change of color tone and brightness, which requires more measurement angles as described above. Further, the information obtained as a result of the measurement is a graph of a spectral reflectance of each angle, a table or chart diagram that arranges color information of each angle, or the like, and it is difficult to make a comprehensive determination by integrating measurement results of all angles.

Thus, the present invention is made in consideration of the above problem, and the purpose of the present invention is to provide a surface property indexing apparatus, a surface property indexing method, and a program, which are capable of integratively indexing a surface property of a measured object, by utilizing measurement results at a plurality of illumination wavelengths and a plurality of measurement angles.

Solution to Problem

In order to solve the above problem, according to an aspect of the present invention, there is provided a surface property indexing apparatus including: a measurement device configured to radiate an illumination light on a surface of a measured object, and capture an image of a reflected light of the illumination light on the surface of the measured object, while selecting a wavelength, to generate a plurality of captured images; and an arithmetic processing apparatus configured to index a surface property of the measured object on the basis of the plurality of captured images generated by the measurement device. The measurement device includes an illumination light source configured to radiate the illumination light on the surface of the measured object, an image capturing device configured to capture images of the reflected light from the surface of the measured object, and a wavelength selection mechanism configured to select a wavelength of the reflected light that forms an image in the image capturing device. The captured images generated by the image capturing device are images of the same wavelength of the reflected light that forms the images in the image capturing device and of different reflection angles of the reflected light that forms the images in the image capturing device in a direction corresponding to a longitudinal direction of the measured object in the captured images. The measurement device generates a plurality of the captured images corresponding to a plurality of different wavelengths respectively with respect to a same view field of the measured object, and sequentially generates a plurality of sets of the plurality of captured images, while shifting the view field. The arithmetic processing apparatus includes an image reconstructing unit configured to perform reconstruction by utilizing the plurality of sets of the plurality of captured images, to generate a processing target image having a common wavelength of the reflected light and a common reflection angle of the reflected light and composed of pixels corresponding to different view field positions of the measured object, for each combination of a wavelength of the reflected light and a reflection angle of the reflected light, and a surface property indexing unit configured to index a surface property of the measured object on the basis of a plurality of the processing target images generated by the image reconstructing unit.

The arithmetic processing apparatus may further include a feature value converting unit that converts a feature value extracted from the plurality of processing target images. The feature value converting unit may convert the feature value in a first feature value space specified by the wavelength and the reflection angle of the reflected light, which is extracted from the plurality of processing target images, to a feature value in a second feature value space of a smaller number of dimensions than the first feature value space. The surface property indexing unit may index a surface property of the measured object, by utilizing the feature value in the second feature value space.

The feature value converting unit may perform principal component analysis to the feature value in the first feature value space, to compress the number of dimensions of the first feature value space to the number of dimensions of the second feature value space.

The measurement device may capture an image of the surface of the measured object, at a position where the surface of the measured object curves.

The wavelength selection mechanism may be a liquid crystal tunable filter or an acoust-optic tunable filter.

The feature value extracted from the plurality of processing target images may be at least one of a brightness value at a pixel position of interest, a variation degree of brightness values of pixels that are positioned around the pixel position of interest, including the brightness value at the pixel position of interest, and a gradient of the brightness values of the pixels that are positioned around the pixel position of interest, including the brightness value at the pixel position of interest.

The measured object may be titanium or titanium alloy, a stainless steel plate, a color coated steel plate, a laminated steel plate, or a plated steel plate.

In order to solve the above problem, according to another aspect of the present invention, there is provided a surface property indexing method including: a measurement step of measuring a surface of a measured object by a measurement device that radiates an illumination light on the surface of the measured object and captures an image of a reflected light of the illumination light on the surface of the measured object while selecting a wavelength of the reflected light that forms an image in an image capturing device, and generating a plurality of captured images of the same wavelength of the reflected light that forms the image in the image capturing device and of different reflection angles of the reflected light that forms the image in the image capturing device in a direction corresponding to a longitudinal direction of the measured object in the captured images, for a same view field of the measured object, corresponding to a plurality of different wavelengths respectively, and generating a plurality of sets of the plurality of captured images sequentially while shifting the view field; an image reconstructing step of performing reconstruction by utilizing the plurality of sets of the plurality of captured images generated by the measurement device, by an arithmetic processing apparatus that indexes a surface property of the measured object, to generate a processing target image having a common wavelength of the reflected light and a common reflection angle of the reflected light and composed of pixels corresponding to different view field positions of the measured object, for each combination of a wavelength of the reflected light and a reflection angle of the reflected light; and a surface property indexing step of indexing the surface property of the measured object on the basis of a plurality of the processing target images generated in the image reconstructing step, by the arithmetic processing apparatus.

The surface property indexing method may further include: a feature value converting step of converting a feature value extracted from the plurality of processing target images, between the image reconstructing step and the surface property indexing step. In the feature value converting step, the feature value in a first feature value space specified by the wavelength and the reflection angle of the reflected light, which is extracted from the plurality of processing target images, may be converted to a feature value in a second feature value space of a smaller number of dimensions than the first feature value space. In the surface property indexing step, the surface property of the measured object may be indexed, by utilizing the feature value in the second feature value space.

In the feature value converting step, principal component analysis may be performed to the feature value in the first feature value space, to compress the number of dimensions of the first feature value space to the number of dimensions of the second feature value space.

The measurement device may capture an image of the surface of the measured object at a position where the surface of the measured object curves.

The feature value extracted from the plurality of processing target images may be at least one of a brightness value at a pixel position of interest, a variation degree of brightness values of pixels that are positioned around the pixel position of interest, including the brightness value at the pixel position of interest, and a gradient of the brightness values of the pixels that are positioned around the pixel position of interest, including the brightness value at the pixel position of interest.

The measured object may be titanium or titanium alloy, a stainless steel plate, a color coated steel plate, a laminated steel plate, or a plated steel plate.

In order to solve the above problem, according to still another aspect of the present invention, there is provided a program for causing a computer that is capable of communicating with each other with a measurement device that radiates an illumination light on a surface of a measured object, and captures an image of a reflected light of the illumination light on the surface of the measured object while selecting a wavelength of the reflected light that forms an image in an image capturing device, and thereby generates a plurality of captured images of the same wavelength of the reflected light that forms the image in the image capturing device and of different reflection angles of the reflected light that forms the image in the image capturing device in a direction corresponding to a longitudinal direction of the measured object in the captured images, for a same view field of the measured object, corresponding to a plurality of different wavelengths respectively, and sequentially generates a plurality of sets of the plurality of captured images while shifting the view field, to implement: an image reconstruction function of performing reconstruction by utilizing the plurality of sets of the plurality of captured images, to generate a processing target image having a common wavelength of the reflected light and a common reflection angle of the reflected light and composed of pixels corresponding to different view field positions of the measured object, for each combination of a wavelength of the reflected light and a reflection angle of the reflected light; and a surface property indexing function of indexing a surface property of the measured object on the basis of a plurality of the processing target images generated by the image reconstruction function.

The program may cause the computer to further implement a feature value conversion function of converting a feature value extracted from the plurality of processing target images. The feature value conversion function may convert the feature value in a first feature value space specified by the wavelength and the reflection angle of the reflected light, which is extracted from the plurality of processing target images, to a feature value in a second feature value space of a smaller number of dimensions than the first feature value space. The surface property indexing function may index a surface property of the measured object, by utilizing the feature value in the second feature value space.

The feature value conversion function may perform principal component analysis to the feature value in the first feature value space to compress the number of dimensions of the first feature value space to the number of dimensions of the second feature value space.

The feature value extracted from the plurality of processing target images may be at least one of a brightness value at a pixel position of interest, a variation degree of brightness values of pixels that are positioned around the pixel position of interest, including the brightness value at the pixel position of interest, and a gradient of the brightness values of the pixels that are positioned around the pixel position of interest, including the brightness value at the pixel position of interest.

Advantageous Effects of Invention

As described above, according to the present invention, a plurality of captured images generated by the measurement device are reconstructed to generate a plurality of processing target images of a common wavelength of reflected light and a common reflection angle of reflected light, and a surface property is indexed by using these processing target images, and thereby the surface property of a measured object can be indexed integratively.

BRIEF DESCRIPTION OF DRAWINGS

FIG. 6 is an explanatory diagram for describing a measurement device included in a surface property indexing apparatus according to the embodiment.

DESCRIPTION OF EMBODIMENTS

Hereinafter, (a) preferred embodiment(s) of the present invention will be described in detail with reference to the appended drawings. In this specification and the drawings, elements that have substantially the same function and structure are denoted with the same reference signs, and repeated explanation is omitted.

(With Regard to Configuration of Surface Property Indexing Apparatus)

Figure 1:
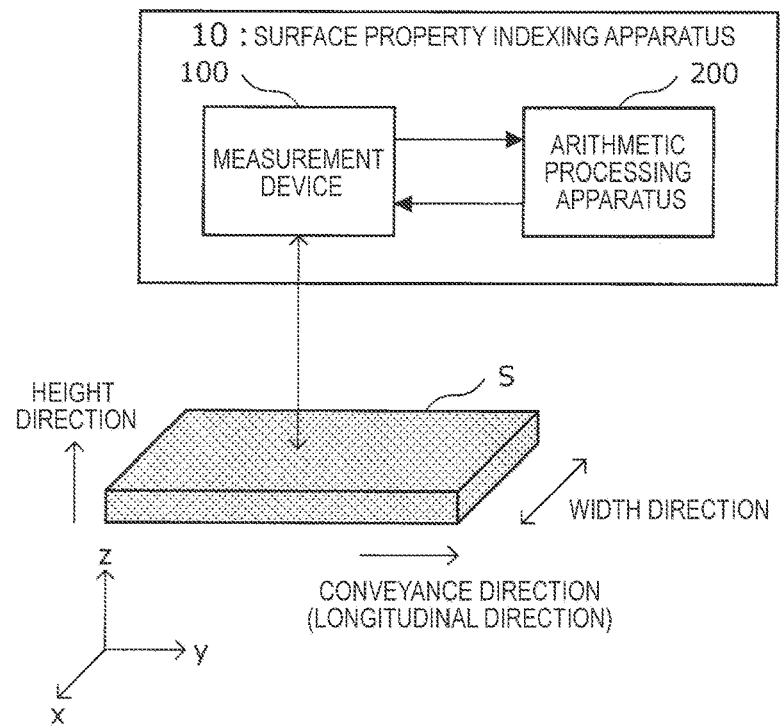
FIG. 1 is a block diagram illustrating an example of a configuration of a surface property indexing apparatus according to a first embodiment of the present invention.

First, an overall configuration of a surface property indexing apparatus according to a first embodiment of the present invention will be described, with reference to FIG. 1. FIG. 1 is an explanatory diagram illustrating one exemplary configuration of the surface property indexing apparatus according to the present embodiment.

The surface property indexing apparatus according to the present embodiment is an apparatus that indexes a surface property of a measured object, by utilizing a strip-shaped illumination light.

The measured object as a measurement target of the surface property indexing apparatus is not limited particularly, and is for example various types of metal objects such as non-ferrous metal such as titanium and titanium alloy, a stainless steel plate, a color coated steel plate, a laminated steel plate, a plated steel plate, and the like.

In the following, an example of indexing a surface property of a metal strip S such as a steel plate conveyed on a predetermined conveyor line will be described. Here, the metal strip S is conveyed toward a certain direction on a conveyor line which is not illustrated in the drawings, and the longitudinal direction of the metal strip S is also referred to as conveyance direction.

A surface property indexing apparatus 10 mainly includes a measurement device 100 and an arithmetic processing apparatus 200, as illustrated in FIG. 1.

The measurement device 100 is a device that radiates a strip-shaped illumination light on a surface of the metal strip S which is a measured object, and measures a reflected light of the illumination light which is reflected on a metal strip surface, and generates brightness data (i.e., a captured image) of the reflected light, under control by the arithmetic processing apparatus 200. The measurement device 100 outputs the generated brightness data of the reflected light to the arithmetic processing apparatus 200.

The arithmetic processing apparatus 200 controls a measurement process of the measured object by the measurement device 100, and acquires the brightness data of the reflected light which is generated by the measurement device 100, and performs data processing, which is described in detail below, to the acquired brightness data, and thereby indexes the surface property of the measured object.

The measurement process of the measured object surface by the measurement device 100 and a calculation process of a surface shape by the arithmetic processing apparatus 200 can be performed in real time along with conveyance of the measured object (for example, the metal strip S). A user of the surface property indexing apparatus 10 uses a measurement result output from the surface property indexing apparatus 10 (in more detail, the arithmetic processing apparatus 200), to recognize in real time the surface property of the metal strip S which is the measured object.

In the following, each of the measurement device 100 and the arithmetic processing apparatus 200 will be described in detail.

(With Regard to Measurement Device)

Next, the measurement device 100 according to the present embodiment will be described in detail with reference to FIGS. 2 to 6. FIGS. 2 to 6 are explanatory diagrams for describing the measurement device 100 according to the present embodiment.

Figure 2:
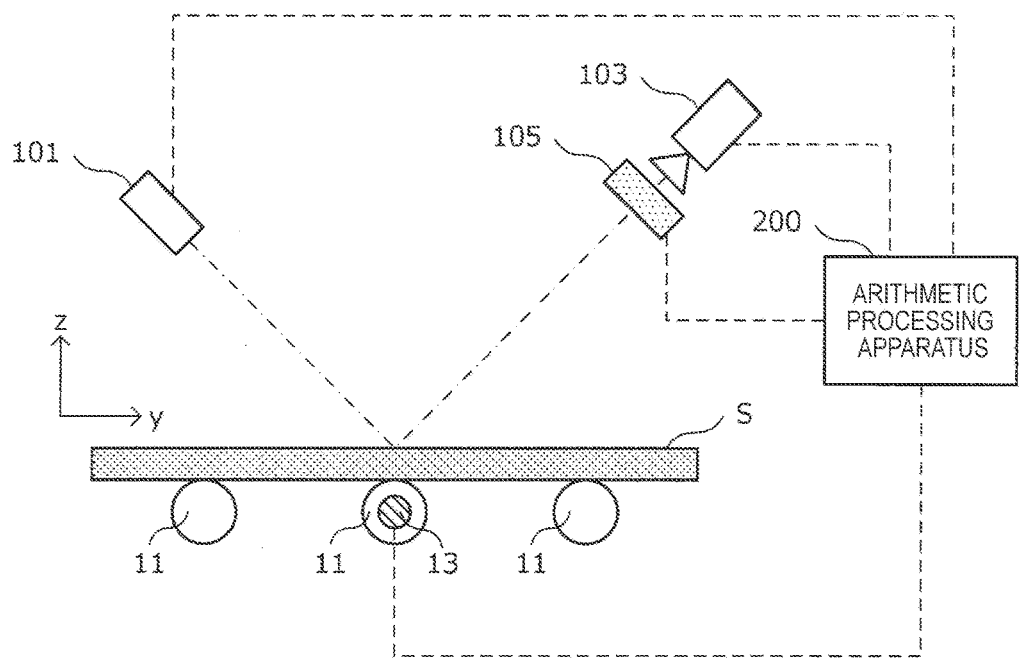
FIG. 2 is an explanatory diagram for describing a measurement device included in a surface property indexing apparatus according to the embodiment.

FIG. 2 is a schematic diagram of the measurement device 100 according to the present embodiment, as seen from a lateral direction of the metal strip S which is the measured object. The measurement device 100 according to the present embodiment includes at least an illumination light source 101, a two-dimensional camera 103 which is an example of an image capturing device, and a wavelength selection mechanism 105, as illustrated in FIG. 2. The illumination light source 101, the two-dimensional camera 103, and the wavelength selection mechanism 105 are fixed by publicly known means (not depicted), so as not to change their set positions. Also, operations of the illumination light source 101, the two-dimensional camera 103, and the wavelength selection mechanism 105 are controlled by the arithmetic processing apparatus 200 which is described later.

Also, the metal strip S of the measured object is assumed to be conveyed toward the positive direction of y direction in the drawing by conveyance rolls 11. Also, an encoder 13 is provided in at least a part of the conveyance rolls 11, and each time the conveyance rolls 11 rotate a predetermined angle (i.e., each time the metal strip S moves a predetermined distance), a pulse signal (a PLG signal) is output to the arithmetic processing apparatus 200.

The illumination light source 101 radiates a strip-shaped illumination light to the surface of the metal strip S which is the measured object. Here, it is preferable that the illumination light radiated to the surface of the metal strip S be white light. With regard to the light source itself, any light source can be utilized, if the light source is capable of radiating illumination light over the almost entire area of the metal strip S in the width direction. As this light source, a rod-like LED light can be utilized, and light of a halogen light source collected by a fiber light guide or the like into a strip shape can be used as well, for example.

Also, it is preferable that the illumination light source 101 be installed obliquely with respect to a normal direction (z axis direction in FIG. 2) of the metal strip surface (in other words, installed in such a manner that the optical axis of the illumination light source 101 and the normal direction of the metal strip surface form a predetermined angle other than 90°). The installation angle of the illumination light source 101 (the angle formed between the optical axis of the illumination light source 101 and the normal direction of the metal strip surface) is not limited particularly, and is preferably approximately 45°, for example.

The two-dimensional camera 103, which is an example of the image capturing device, is a device that is installed obliquely with respect to the surface of the metal strip S of the measured object, and captures an image of the reflected light from the metal strip surface which has transmitted through the wavelength selection mechanism 105 described later, and generates brightness data of the reflected light.

Here, the installation angle of the two-dimensional camera 103 (the angle formed between the optical axis of the two-dimensional camera 103 and the normal direction of the metal strip surface) is not limited particularly, and for example may be installed in such a manner that the optical axis of the two-dimensional camera 103 is perpendicular to the metal strip surface, but it is preferable that the two-dimensional camera 103 be installed obliquely with respect to the metal strip surface. A specific value of this oblique installation angle is not limited particularly, but is preferably an angle such that geometric optical regular reflection of the illumination light is included and a longitudinal direction range as large as possible is included in the imaging view field of the two-dimensional camera 103. A reason of this will be described in detail below.

This two-dimensional camera 103 captures an image of the reflected light that has transmitted through the wavelength selection mechanism 105 each time a camera driving pulse is input from the arithmetic processing apparatus 200, and generates captured images as many as the number of input camera driving pulses. A plurality of captured images generated by the two-dimensional camera 103 are output to the arithmetic processing apparatus 200.

The wavelength selection mechanism 105 is a mechanism that selects a wavelength of the reflected light that forms an image in the two-dimensional camera 103, and the transmitted wavelength of the reflected light is controlled by the arithmetic processing apparatus 200. The wavelength selection mechanism 105 switches the transmitted wavelength of the reflected light by changing a specification of the wavelength selection mechanism 105, each time a switching pulse of a transmission wavelength is input from the arithmetic processing apparatus 200. Thus, the wavelength of the reflected light that forms an image in the two-dimensional camera 103 can be continuously changed, by continuously sweeping the transmitted wavelength of the reflected light, for example. Thus, as described later, one captured image can be generated each time the wavelength of the reflected light changes, by synchronizing the wavelength switching timing in the wavelength selection mechanism 105 and the image capturing timing in the two-dimensional camera 103.

This wavelength selection mechanism 105 is not limited particularly, but may be a publicly known optical member. A specific example of this wavelength selection mechanism 105 is a publicly known tunable filter TF, such as a liquid crystal tunable filter (LCTF) or an acoust-optic tunable filter (AOTF).

Figure 3:
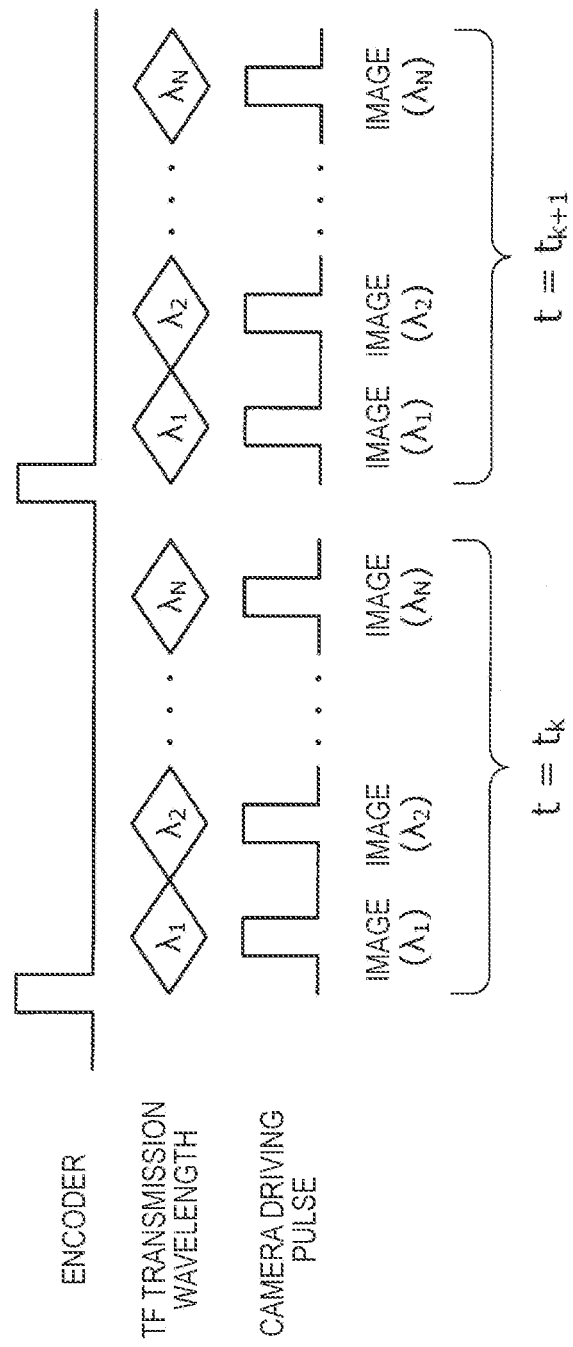
FIG. 3 is an explanatory diagram for describing a measurement device included in a surface property indexing apparatus according to the embodiment.

A control example of the two-dimensional camera 103 and the wavelength selection mechanism 105 by the arithmetic processing apparatus 200, which is described above, will be described with reference to FIG. 3. FIG. 3 is an explanatory diagram for describing an example of drive control of the two-dimensional camera 103 and the wavelength selection mechanism 105.

The measurement device 100 according to the present embodiment captures an image of the surface of the metal strip S that is positioned in the view field of the two-dimensional camera 103, each time the metal strip S is conveyed by a predetermined distance on the conveyor line. When the PLG signal is input into the arithmetic processing apparatus 200 from the encoder 13 provided in the conveyance roll 11 for configuring the conveyor line, the arithmetic processing apparatus 200 outputs a control signal for changing the transmission wavelength to the wavelength selection mechanism 105, and causes the wavelength selection mechanism 105 to switch the transmission wavelength. Also, the arithmetic processing apparatus 200 outputs the camera driving pulse to the two-dimensional camera 103 at a timing the transmission wavelength is switched, and causes the two-dimensional camera 103 to capture an image of the surface of the metal strip S.

In the present embodiment, as illustrated in FIG. 3, wavelengths of N (N≥2) types including $\lambda_1$ to $\lambda_N$ are assumed to be selected by the wavelength selection mechanism 105 configured with the publicly known tunable filter TF. As illustrated in FIG. 3, the camera driving pulse that is synchronized with switching of the transmission wavelength is input into the two-dimensional camera 103, and thereby the two-dimensional camera 103 generates N types of captured images that capture images of the same view field of the surface of the metal strip S, from a captured image that captures an image of the reflected light of the wavelength $\lambda_1$ to a captured image that captures an image of the reflected light of the wavelength $\lambda_N$. Although the metal strip S actually moves at a certain speed, these N types of images can be assumed to capture images of the same view field of the metal strip S surface, if the time taken to select the wavelength is so small as to be disregarded, as compared with the moving speed. Comparing the actual wavelength selection time in the measurement device 100 and the actual moving speed of the metal strip S in the present embodiment, the wavelength selection time is so small as to be disregarded, and thus the N types of images generated by the measurement device 100 can be considered as capturing images of the same view field. Each captured image generated as described above can be utilized as a two-dimensional spectral image at a certain wavelength $\lambda$. Subsequently, when the PLG signal is input into the arithmetic processing apparatus 200 from the encoder 13, N types of captured images are generated with respect to the surface after the metal strip S proceeds by a predetermined distance, in the same way.

This image capturing process is performed, so that the measurement device 100 according to the present embodiment generates a plurality of captured images corresponding to a plurality of different wavelengths respectively, for the same view field of the measured object, and generates a plurality of sets of a plurality of captured images sequentially, while shifting the view field.

Next, with reference to FIG. 4, a feature of the captured image generated by the measurement device 100 will be described. In the following, an example in which the optical axis of the two-dimensional camera 103 is inclined with respect to the normal direction of the metal strip surface, as illustrated in FIG. 4 for example, will be described.

Figure 4:
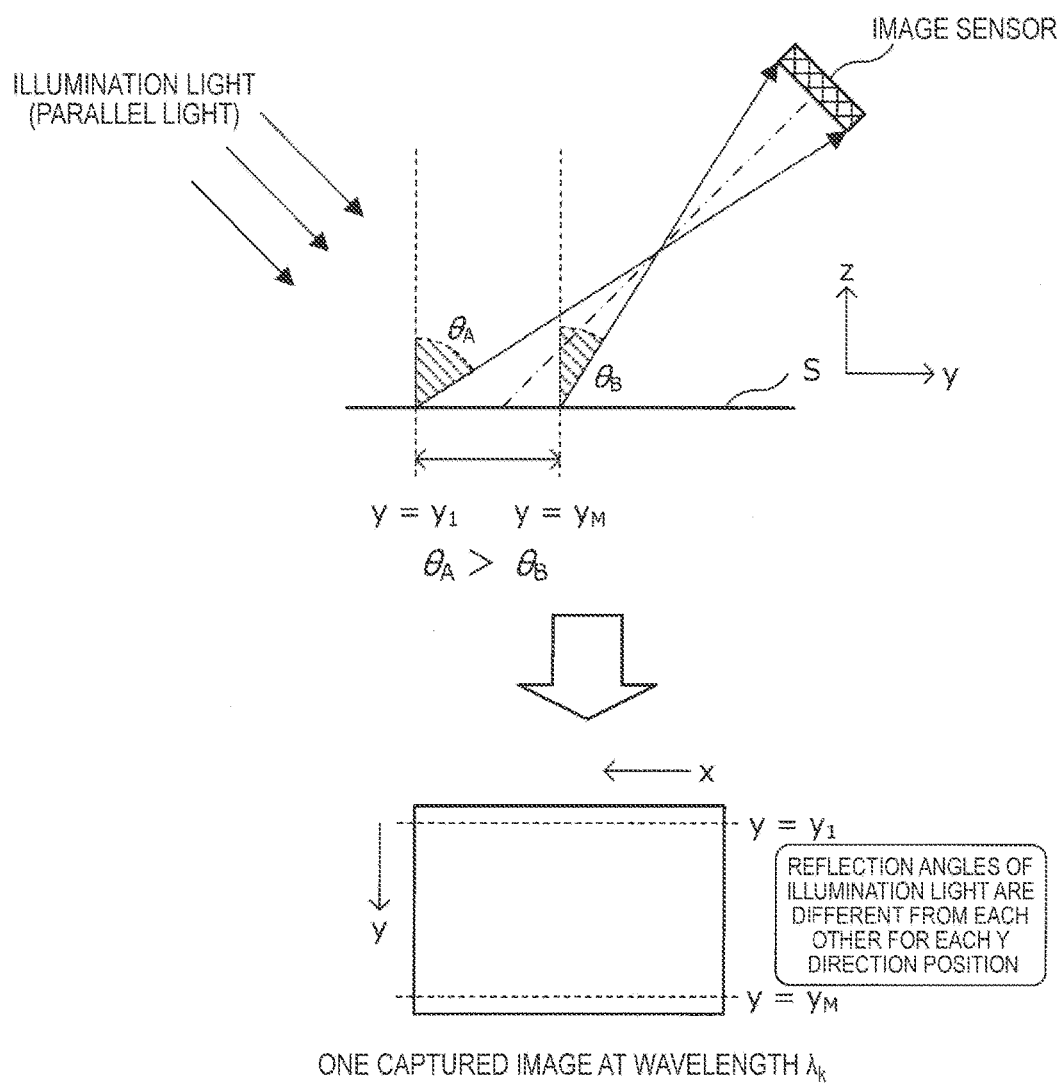
FIG. 4 is an explanatory diagram for describing a measurement device included in a surface property indexing apparatus according to the embodiment.

As illustrated in FIG. 4, a part of the metal strip S having a predetermined area size is positioned in the imaging view field, according to a number of characteristics of a lens and an image sensor included in the two-dimensional camera 103. Here, as illustrated in FIG. 4, the longitudinal direction (y axis direction in the drawing) of the metal strip S which is the measured object will be considered in the captured image of a certain transmission wavelength $\lambda_k$ (k=1 to N). In this case, as is obvious from the upper side of FIG. 4, the angle (i.e., the reflection angle of the illumination light) $\theta_A$ formed between the direction of forward movement of the reflected light at y=$y_1$ and the normal direction of the metal strip surface and the angle $\theta_B$ formed between the direction of forward movement of the reflected light at y=$y_M$ and the normal direction of the metal strip surface are different from each other. More specifically, as a part is positioned at a remoter place from the image sensor (in other words, a part that is positioned at a more y axis negative direction side), the reflection angle $\theta$ becomes larger. Thus, in the captured image captured by the two-dimensional camera 103 according to the present embodiment, the reflection angle of the illumination light differs for each y direction position, as illustrated in the lower side of FIG. 4. On the other hand, the reflection angle is considered to be constant, with respect to the width direction (x axis direction in the drawing) of the metal strip S which is the measured object, as illustrated in the lower side of FIG. 4. Hence, with regard to a pixel group that is positioned on a line that is parallel to the x axis at a longitudinal direction position y, the reflection angle is constant at a certain angle according to the longitudinal direction position y.

Here, as is obvious by considering with reference to FIG. 4, when the installation angle of the two-dimensional camera 103 is perpendicular to the metal strip surface, the situation of the change of the reflection angle in the captured image becomes symmetric with respect to an intersection line between the optical axis of the two-dimensional camera 103 and the metal strip surface. Thus, in order to include more contribution of reflection angle $\theta$ into the captured image, it is preferable to install the two-dimensional camera 103 in an inclined manner to the normal direction of the metal strip surface, and it is more preferable to locate the two-dimensional camera 103 in such a manner that the regular reflection of the illumination light is positioned at a vicinity of the end portion of the imaging view field in the longitudinal direction (a vicinity of y=$y_1$ or y=$y_M$ in the lower side of FIG. 4).

Figure 5:
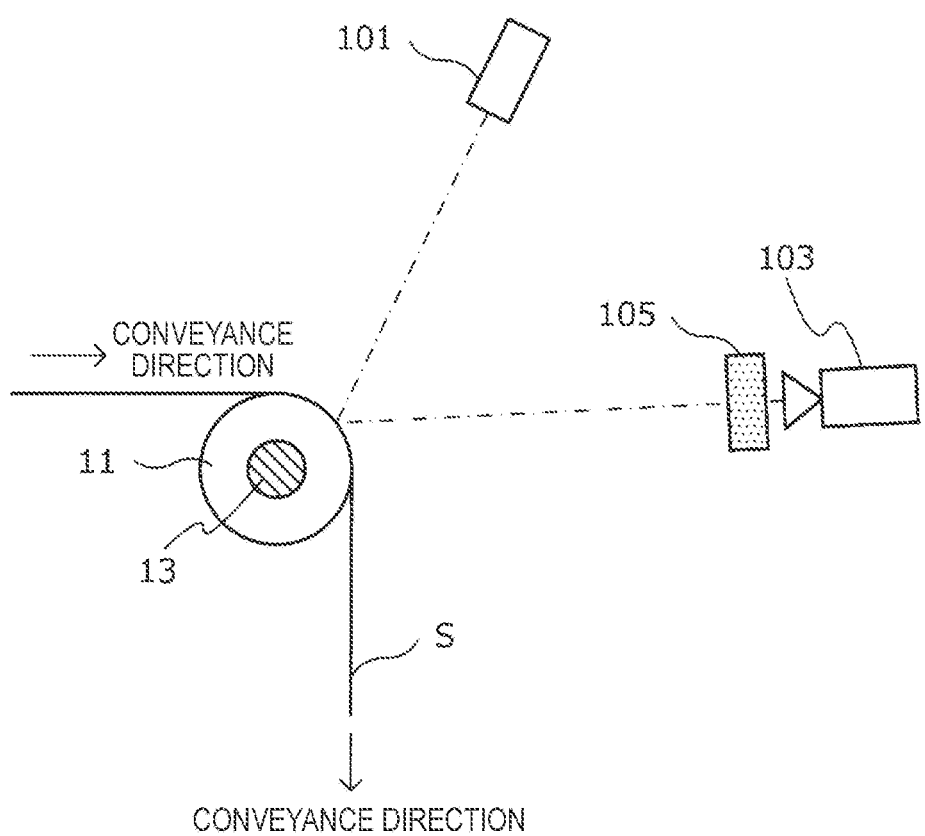
FIG. 5 is an explanatory diagram for describing a measurement device included in a surface property indexing apparatus according to the embodiment.

Here, in FIGS. 2 and 4, description has been made taking an example of a case in which the surface of the metal strip S of the measured object is horizontal, but it is more preferable to execute the measurement process at a position where the surface of the metal strip S of the measured object curves, as illustrated in FIG. 5. The detail of the position where the surface of the metal strip S curves is not limited particularly, and is for example a location (roll wound portion) where the metal strip S is wound around the conveyance roll 11 and the conveyance direction changes, as illustrated in FIG. 5. More contribution of the reflection angle $\theta$ is included in the captured image, as illustrated in FIG. 6, by performing the measurement on this curved surface.

That is, it is found that, as illustrated in the lower side of FIG. 6, when the surface of the metal strip S curves, the reflection angle $\theta$ has a larger value. Thus, a larger angle change occurs as compared with a case in which the surface of the metal strip S is horizontal as illustrated in the upper side of FIG. 6, and as a result more contribution of the reflection angle $\theta$ is included in the captured image.

In the above, the measurement device 100 according to the present embodiment has been described in detail, with reference to FIGS. 2 to 6.

(With Regard to Arithmetic Processing Apparatus)

Figure 7:
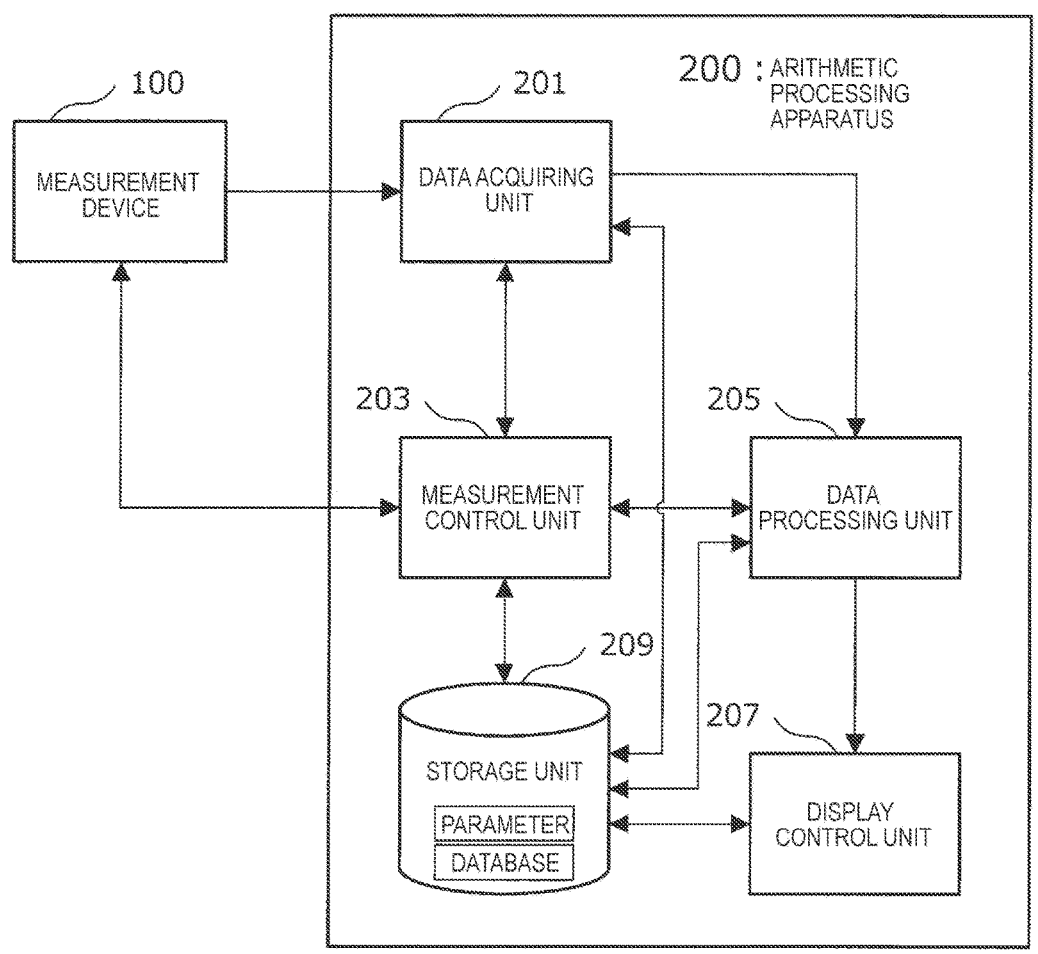
FIG. 7 is a block diagram illustrating an example of a configuration of an arithmetic processing apparatus included in a surface property indexing apparatus according to the embodiment.

Next, with reference to FIG. 7, the configuration of the arithmetic processing apparatus 200 according to the present embodiment will be described in detail. FIG. 7 is a block diagram illustrating an example of the configuration of the arithmetic processing apparatus 200 according to the present embodiment.

The arithmetic processing apparatus 200 according to the present embodiment is an apparatus that indexes the surface property of the measured object on the basis of a measured value of brightness (i.e., the brightness data) of a reflected light by the measurement device 100. This arithmetic processing apparatus 200 mainly includes a data acquiring unit 201, a measurement control unit 203, a data processing unit 205, a display control unit 207, and a storage unit 209, as illustrated in FIG. 7.

For example, the data acquiring unit 201 is configured with a central processing unit (CPU), a read only memory (ROM), a random access memory (RAM), and a communication device. The data acquiring unit 201 acquires brightness data of the reflected light (i.e., substantial data of the captured image) which is generated by the measurement device 100 and output from the measurement device 100, and sends the brightness data to the data processing unit 205 described later. The brightness data acquired by the data acquiring unit 201 is a plurality of sets of (a plurality of view fields of) brightness data including a plurality of captured images of the same view field, as described above. Also, the data acquiring unit 201 may contain the acquired brightness data of the reflected light as history information in the storage unit 209 described later, in association with time point information relevant to date and time at which the data is acquired.

The measurement control unit 203 is configured with a CPU, a ROM, a RAM, and a communication device, for example. The measurement control unit 203 executes measurement control of the metal strip S by the measurement device 100 according to the present embodiment. In more detail, the measurement control unit 203 sends a control signal for starting radiation of the illumination light, to the illumination light source 101, when starting the measurement of the metal strip S.

Also, when the illumination light source 101 starts the radiation of each illumination light on the surface of the metal strip 5, the measurement control unit 203 sends various types of control signals described in FIG. 3, to the wavelength selection mechanism 105 and the two-dimensional camera 103, on the basis of a PLG signal which is periodically sent from the encoder 13 provided in a drive mechanism for changing a relative position between the metal strip S and the measurement device 100 (for example, a PLG signal output each time the metal strip S moves 1 mm).

Thereby, the measurement device 100 can generate a captured image which is the measurement data at each position of the metal strip S in the conveyance direction.

For example, the data processing unit 205 is configured with a CPU, a ROM, a RAM, and a communication device. The data processing unit 205 utilizes the captured image of the reflected light generated by the measurement device 100 to perform data processing described below to the captured image of each reflected light, and thereby indexes the surface property of the metal strip S. When ending the indexing process of the surface property of the metal strip S, the data processing unit 205 sends information of the obtained processing result to the display control unit 207.

Note that this data processing unit 205 will be described in detail below.

For example, the display control unit 207 is configured with a CPU, a ROM, a RAM, and an output device. The display control unit 207 executes a display control when displaying various types of processing results including the indexing result of the surface property of the metal strip S, which is sent from the data processing unit 205, on an output device such as a display included in the arithmetic processing apparatus 200 and an output device provided outside the arithmetic processing apparatus 200 or the like. Thereby, the user of the surface property indexing apparatus 10 can recognize on site various types of processing results such as the indexing result of the surface property of the metal strip S.

The storage unit 209 is configured with a RAM and a storage device included in the arithmetic processing apparatus 200 according to the present embodiment, for example. In the storage unit 209, various parameters and process intermediate progresses that the arithmetic processing apparatus 200 according to the present embodiment needs to save when executing some sort of process, various types of databases and programs, or the like are recorded as appropriate. With regard to this storage unit 209, the data acquiring unit 201, the measurement control unit 203, the data processing unit 205, the display control unit 207, and the like can execute a data read/write process freely.

<With Regard to Data Processing Unit>

Figure 8:
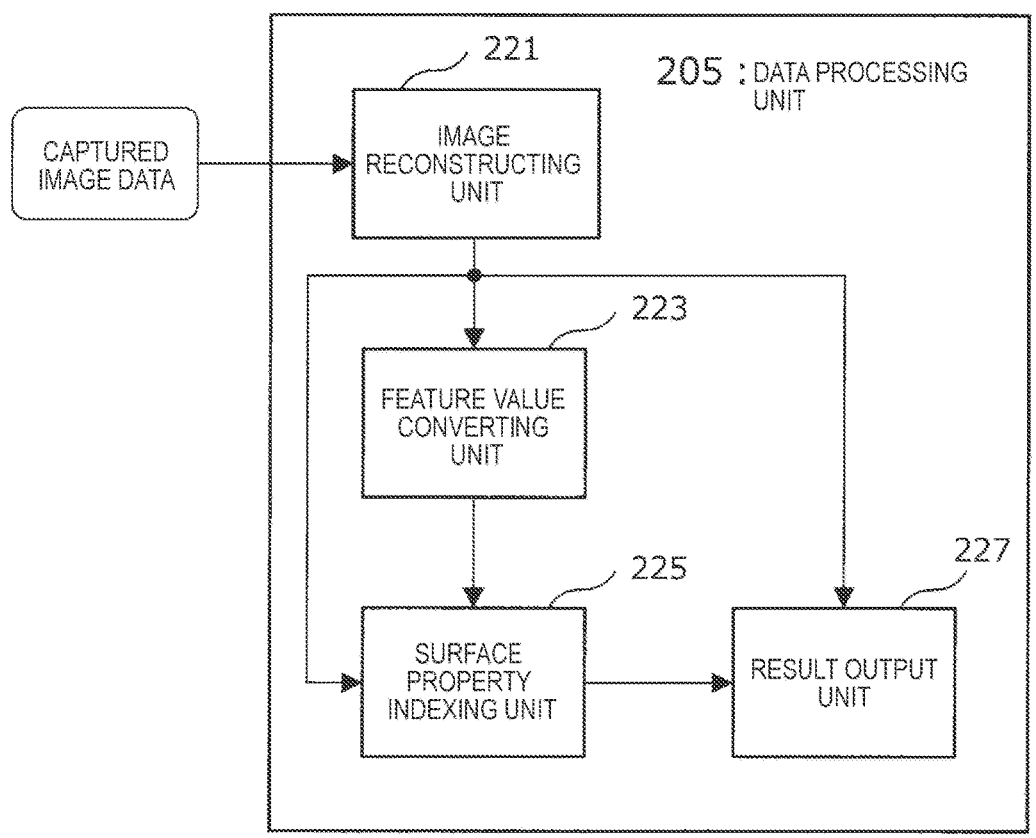
FIG. 8 is a block diagram illustrating an example of a configuration of a data processing unit included in an arithmetic processing apparatus according to the embodiment.
Figure 9:
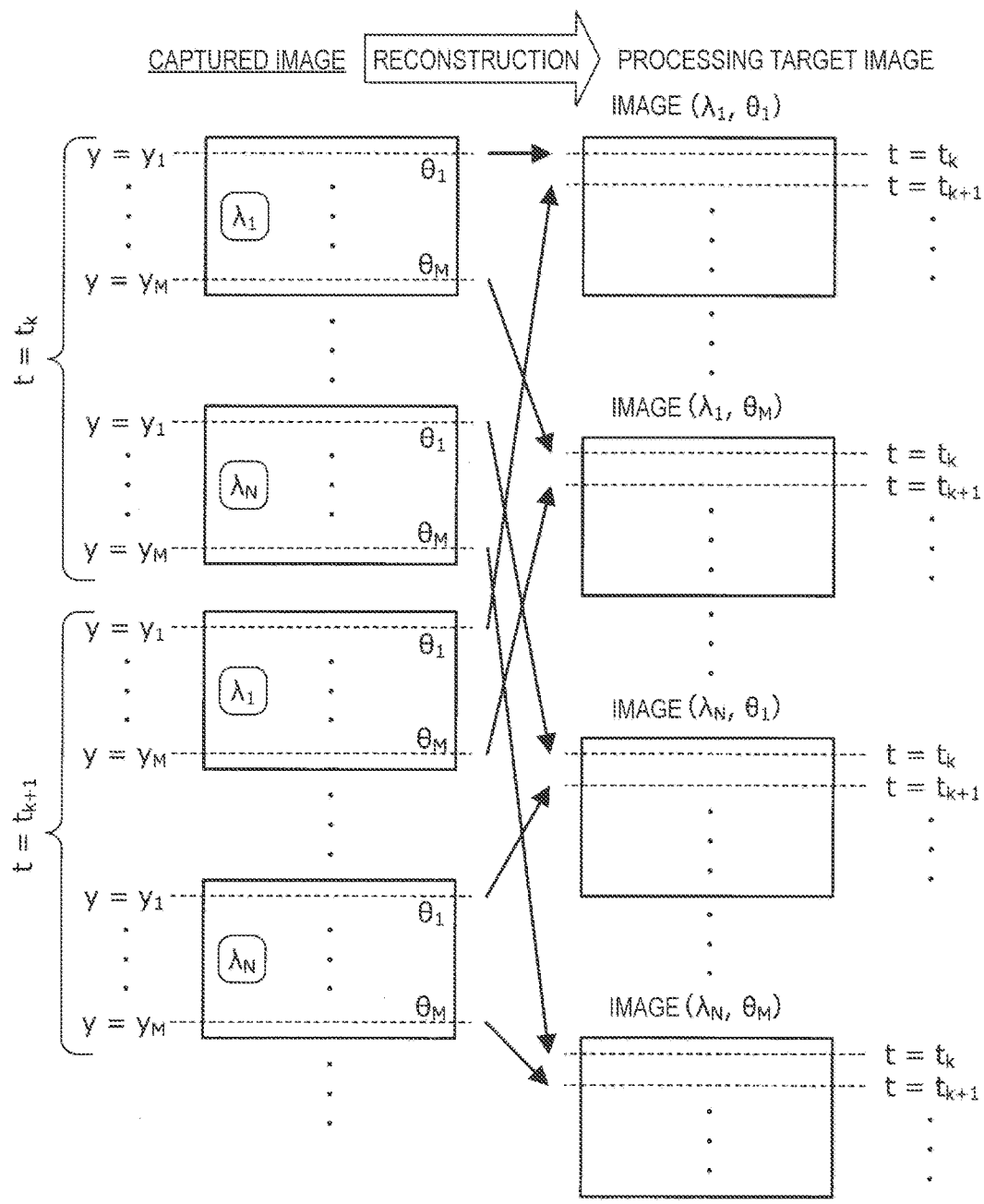
FIG. 9 is an explanatory diagram for describing a reconstruction process of a captured image according to the embodiment.
Figure 10:
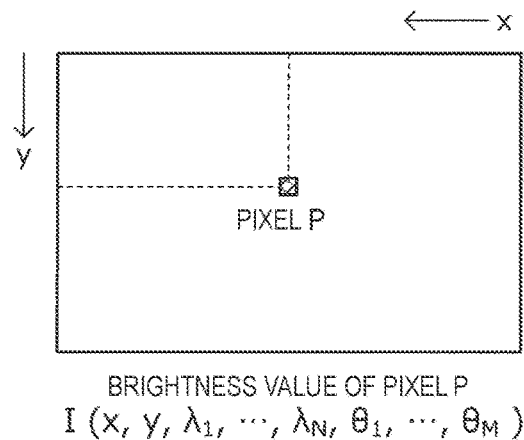
FIG. 10 is an explanatory diagram for describing a reconstruction process of a captured image according to the embodiment.
Figure 11:
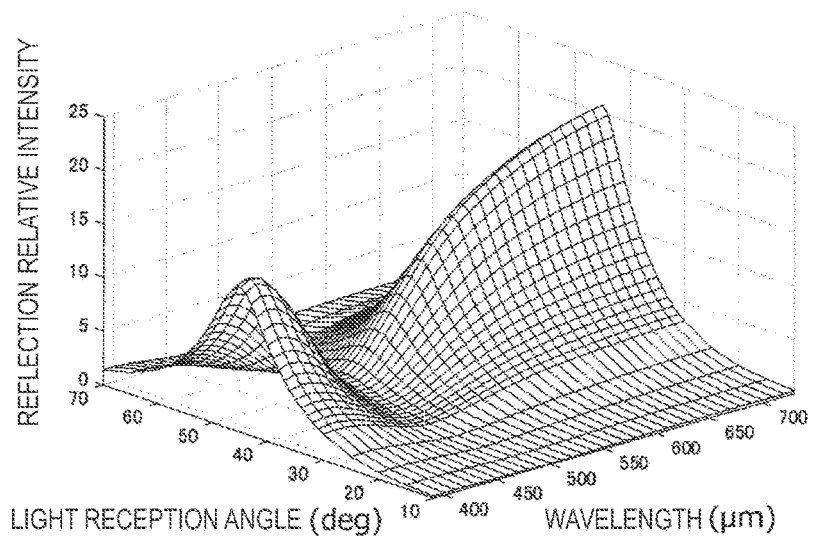
FIG. 11 is an explanatory diagram for describing an advantage of using a processing target image according to the embodiment.
Figure 12A:
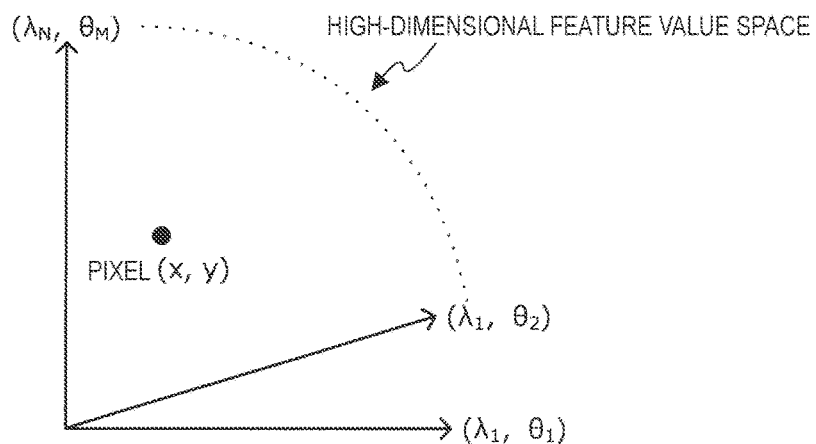
FIG. 12A is an explanatory diagram for describing a conversion process of a feature value and an indexing process of a surface property according to the embodiment.

Next, an example of the configuration of the data processing unit 205 included in the arithmetic processing apparatus 200 according to the present embodiment will be described in detail, with reference to FIGS. 8 to 13. FIG. 8 is a block diagram illustrating an example of the configuration of the data processing unit included in the arithmetic processing apparatus according to the present embodiment. FIG. 9 is an explanatory diagram for describing a reconstruction process of the captured image according to the present embodiment. FIG. 10 is an explanatory diagram for describing the reconstruction process of the captured image according to the present embodiment. FIG. 11 is an explanatory diagram for describing the advantage of using a processing target image according to the present embodiment. FIGS. 12A to 12D are explanatory diagrams for describing a conversion process of a feature value and an indexing process of a surface property according to the present embodiment. FIG. 13 is an explanatory diagram for describing an example of another feature value according to the present embodiment.

The data processing unit 205 according to the present embodiment is a processing unit that indexes the surface property of the metal strip S of the measured object, by utilizing the data of captured images (a plurality of sets of brightness data) acquired by the data acquiring unit 201. This data processing unit 205 includes an image reconstructing unit 221, a feature value converting unit 223, a surface property indexing unit 225, and a result output unit 227, as illustrated in FIG. 8.

For example, the image reconstructing unit 221 is configured with a CPU, a ROM, and a RAM. The image reconstructing unit 221 reconstructs a plurality of sets of captured images, by utilizing a plurality of sets of a plurality of captured images generated by the measurement device 100. Thereby, the image reconstructing unit 221 generates a processing target image having a common wavelength of reflected light and a common reflection angle of reflected light and composed of pixels corresponding to different view field positions of the measured object, for each combination of wavelength of reflected light and reflection angle of reflected light. In the following, an image reconstruction process in this image reconstructing unit 221 will be described specifically with reference to FIG. 9.

As described above, one captured image generated by the measurement device 100 is an image when the wavelength of the reflected light is $\lambda_j$ (j=1 to N), and the reflection angles differ from each other in the direction corresponding to the longitudinal direction of the measured object in the captured image. In the following description, as illustrated in the left side of FIG. 9, the direction corresponding to the longitudinal direction of the measured object of the captured image is referred to as y direction. In this case, the captured image is assumed to be composed of the pixels associated with $y=y_1$ to $y_M$, and the reflection angle corresponding to the position of $y=y_l$ is set as $\theta_1$, and the reflection angle corresponding to the position of $y=y_M$ is set as $\theta_M$.

As described above, the measurement device 100 generates N captured images of a common wavelength $\lambda_j$ (j=1 to N) of the reflected light at a certain timing $t=t_k$, and generates N captured images of a common wavelength $\lambda_j$ (j=1 to N) of the reflected light at a subsequent timing $t=t_{k+1}$. Upon acquiring data of these captured images, the image reconstructing unit 221 first extracts a line of pixels (a line of pixels having the same y coordinate, in FIG. 9) of common (wavelength $\lambda_j$, reflection angle $\theta_l$) (j=1 to N, l=1 to M), from each captured image. Thereafter, the image reconstructing unit 221 rearranges the extracted pixel lines in the order of image capturing timing t, and generates a processing target image illustrated in the right side of FIG. 9. As a result, in the example illustrated in FIG. 9, N captured images generated in each image capturing timing t are reconstructed, and as a whole N×M processing target images of common ($\lambda_j$, $\theta_l$) (j=1 to N, l=1 to M) are generated.

Here, the size of the processing target image can be decided as appropriate. For example, when the longitudinal direction (y direction) of one processing target image is composed of H pixels, N×M processing target images are generated by utilizing images ($\lambda_1$) to ($\lambda_N$) generated during $t=t_k$ to $t_{k+H-1}$.

In each processing target image generated as described above, the brightness values of the pixels that compose the processing target image are associated with four parameters including the wavelength $\lambda$ and the reflection angle $\theta$ of the reflected light in addition to the position coordinates of the pixel, as schematically illustrated in FIG. 10.

Also, the number of pixel lines that are extracted from one captured image may be pixel by pixel, and may be such that a plurality of pixels are extracted at a time to be utilized in one processing target image. The spatial resolution of the generated processing target image in the longitudinal direction is specified according to the number of pixel lines that are extracted from one captured image. This process is executed to thoroughly generate an image of a higher spatial resolution on the entire measurement target surface as compared with a widely used spectrophotometric colorimeter.

The image reconstructing unit 221 outputs a plurality of processing target images generated in this way, to the feature value converting unit 223 described later. Also, when the feature value converting unit 223 does not execute a conversion process of a feature value which is described later, the image reconstructing unit 221 may output the generated processing target images to the surface property indexing unit 225 described later. Further, the image reconstructing unit 221 may output the generated processing target images to the result output unit 227 described later, to report the reconstructed processing target image itself to a user.

Here, with reference to FIG. 11, the advantage of utilizing the processing target image generated by the image reconstructing unit 221 will be described simply.

When a diffracted light from the measured object is utilized to make some sort of determination for the surface of the measured object on the basis of the measurement result by utilizing the light from the surface of the measured object, it is unnecessary to consider the light reception angle dependency of the reflected light from the surface of the measured object. In the same way, when the wavelength dependency of the reflected light intensity is small in the considered measured object, it is sufficient if the wavelength of the reflected light is analyzed only for a specific wavelength band or analyzed roughly by classifying the wavelength of the reflected light into wavelength bands having a certain degree of breadth, as in R component, G component, and B component.

On the other hand, with regard to titanium, titanium alloy, a part of stainless steel plates, or the like, which are mentioned above, the reflected light intensity fluctuates significantly, according to the wavelength of the illumination light used in the measurement and the light reception angle of the reflected light.

FIG. 11 illustrates a situation of change of the reflected light intensity when measuring the reflected light intensity from titanium on which an oxide film exists on its surface, and is a result of measuring reflection relative intensity when an illumination light of parallel light is incident on the above titanium at an incident angle of 45°. FIG. 11 illustrates relative intensity with respect to a reflection intensity measurement value of the standard white plate, as the reflection relative intensity. The light is absorbed at a specific wavelength due to interference in the oxide film that exists on the surface, and the reflection intensity from the titanium on which the oxide film exists on the surface complexly changes according to the wavelength of the illumination light and the light reception angle, as is obvious from FIG. 11.

When the surface property of this measured object is indexed, measuring with the light reception angle fixed to a certain value corresponds to considering a cross section obtained by cutting the three-dimensional graph of FIG. 11 in the flat plane corresponding to the light reception angle of a certain specific value. In the same way, measuring with the wavelength of the illumination light fixed to a certain value corresponds to considering a cross section obtained by cutting the three-dimensional graph of FIG. 11 in the flat plane corresponding to the wavelength of a certain specific value. Thus, when the wavelength of the illumination light and the light reception angle are fixed to certain specific values to index the surface property of the measured object, the complicated influence of the reflected light intensity illustrated in FIG. 11 is unable to be reflected in indexing appropriately.

That is, when indexing the surface property of the measured object whose reflected light intensity largely depends on the light reception angle and the illumination light wavelength as illustrated in FIG. 11, it is important to consider how the brightness value of the reflected light at the pixel position of interest is different from surrounding pixels. Here, an arbitrary combination of measurement conditions including the wavelength of the illumination light and the light reception angle is easily considered by utilizing the processing target image illustrated in FIGS. 9 and 10. Also, comparison between pixels with a fixed measurement condition including the wavelength of the illumination light and the light reception angle can be performed extremely easily, by utilizing this processing target image. As a result, the surface property of the measured object of interest can be indexed more accurately.

Also, the processing target image generated by the reconstruction process illustrated in FIG. 9 retains various information that each captured image intrinsically includes. In other words, in the above processing target image, multidimensional information that respective captured images include is gathered into one pixel. Hence, indexing of the surface property can be performed from various viewpoints, by utilizing the processing target image.

For example, with regard to a color coated steel plate, a laminated steel plate, a plated steel plate, and the like as well, it is envisaged that the surface property is required to be classified more finely, according to diversification of customer needs (for example, classification in more advanced aesthetic level, etc.). In, that case as well, finer classification of the surface property of the measured object can be easily performed by using the processing target image generated by the above reconstruction process.

In the above, the advantage of utilizing the processing target image generated by the image reconstructing unit 221 has been described simply.

For example, the feature value converting unit 223 is configured with a CPU, a ROM, and a RAM. The feature value converting unit 223 utilizes a plurality of processing target images generated by the image reconstructing unit 221, to convert a feature value in a first feature value space specified by the wavelength and the reflection angle of the reflected light, which is extracted from these processing target images, to a feature value in a second feature value space of a smaller number of dimensions than the first feature value space.

In general, the brightness value of a pixel for composing a certain image is associated only with position coordinates of the pixel normally. On the other hand, in the processing target image generated by the image reconstructing unit 221, the brightness values of the pixels that compose the processing target image are associated with four parameters including the wavelength $\lambda$ and the reflection angle $\theta$ of the reflected light in addition to the position coordinates of the pixels, as mentioned before. In other words, the processing target image utilized in the present embodiment includes information relevant to M types of reflection angles and N types of spectroscopy (i.e., wavelengths of the reflected light) at each coordinate (x, y), and therefore the brightness value itself can be considered as the feature value of N×M-dimensional function. Hence, subtle change of color shade, which is unable to be recognized in an RGB image of the past and the like, can be recognized as an image, by utilizing N×M-dimensional information of these respective pixels.

However, when N×M-dimensional information is utilized as it is, a very high-dimensional feature value space is considered, and therefore a load is put on a process, depending on a resource environment that can be utilized by the arithmetic processing apparatus 200 in some cases. Thus, the feature value converting unit 223 converts the brightness value (the feature value of the processing target image) in the feature value space (the first feature value space) specified by the pixel coordinates and N×M-dimensional information of the wavelength and the reflection angle, to the feature value in the feature value space (the second feature value space) of a smaller number of dimensions than the first feature value space. Thereby, indexing of the surface property can be performed in a simple and convenient manner, as compared with a process utilizing the original feature value space.

With respect to the method to convert the feature value space, a publicly known method can be utilized, and the method is not limited particularly. One of such methods is principal component analysis. Information can be compressed into a two-dimensional feature value space including a first principal component and a second principal component for example, by converting the first feature value space specified as a collection of N×M-dimensional information by utilizing the principal component analysis.

Note that this conversion process of the feature value may be performed as necessary, and the conversion process of the feature value is needless to be performed, if the arithmetic processing apparatus 200 can execute the process by utilizing the high-dimensional feature value extracted from the processing target image as it is.

Upon performing the conversion of the feature value as necessary, the feature value converting unit 223 outputs the feature value after the conversion to the surface property indexing unit 225 described later.

For example, the surface property indexing unit 225 is configured with a CPU, a ROM, and a RAM. The surface property indexing unit 225 indexes the surface property of the measured object of interest, on the basis of a plurality of processing target images generated by the image reconstructing unit 221. Here, when the conversion of the feature value is performed by the feature value converting unit 223, the surface property indexing unit 225 may utilize the feature value after the conversion (the feature value in the second feature value space) to perform indexing of the surface property.

Here, the surface property indexed by the surface property indexing unit 225 is not limited particularly, but is for example color tone and brightness on the surface of the measured object and a surface shape including irregularity state or the like on the surface of the measured object, etc.

In addition, the surface property indexing unit 225 not only indexes the surface property of the measured object, but also can determine the surface property of the measured object by utilizing the obtained index.

In the following, a process in the surface property indexing unit 225 will be described with reference to FIGS. 12A to 12D.

The brightness value that composes the processing target image generated by the image reconstructing unit 221 can be utilized as the feature value as described above, and this brightness value itself can be regarded as what the surface property is indexed. This brightness value corresponds to one point in a very high-dimensional feature value space, as schematically illustrated in FIG. 12A. As described above, the surface property indexing unit 225 can handle the brightness value of each pixel for composing the processing target image, as what the surface property of the measured object is indexed.

Figure 12B:
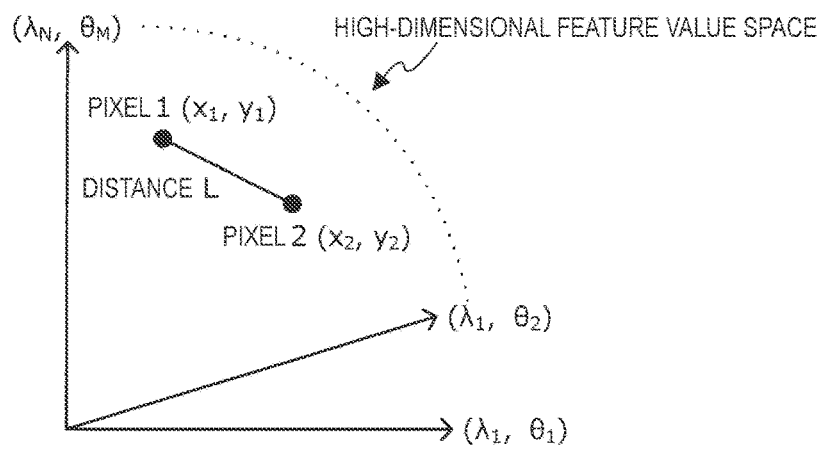
FIG. 12B is an explanatory diagram for describing a conversion process of a feature value and an indexing process of a surface property according to the embodiment.
Figure 13:
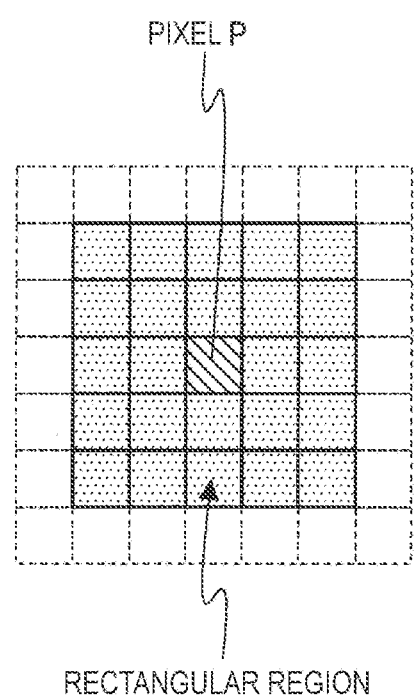
FIG. 13 is an explanatory diagram for describing an example of another feature value according to the embodiment.

Also, the surface property indexing unit 225 may index the surface property of the measured object, by calculating a distance L (for example, L2 norm, etc.) in the feature value space, as schematically illustrated in FIG. 12B, for example.

Figure 12C:
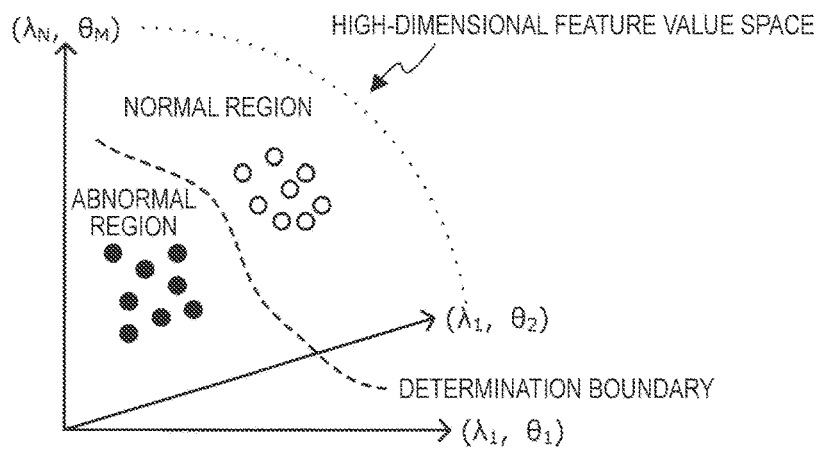
FIG. 12C is an explanatory diagram for describing a conversion process of a feature value and an indexing process of a surface property according to the embodiment.

Here, the surface property indexing unit 225 can also determine the surface property by utilizing the extracted feature value. In this case, as schematically illustrated in FIG. 12C for example, a determination boundary is decided in advance to separate a normal region (normal determination region) and an abnormal region (abnormal determination region) in the feature value space, by a publicly known machine learning technology, a pattern learning technology, or the like, by utilizing a combination of past operation data and its evaluation result as teacher data. Then, the surface property indexing unit 225 can determine the surface property, by determining which one of the normal region and the abnormal region includes the feature value extracted from the processing target image of interest.

This machine learning technology and pattern learning technology are not limited particularly, but are for example methods such as constructing a support vector classifier (SVC) by utilizing teacher data, creating a decision tree and a decision table by utilizing teacher data, and the like.

Figure 12D:
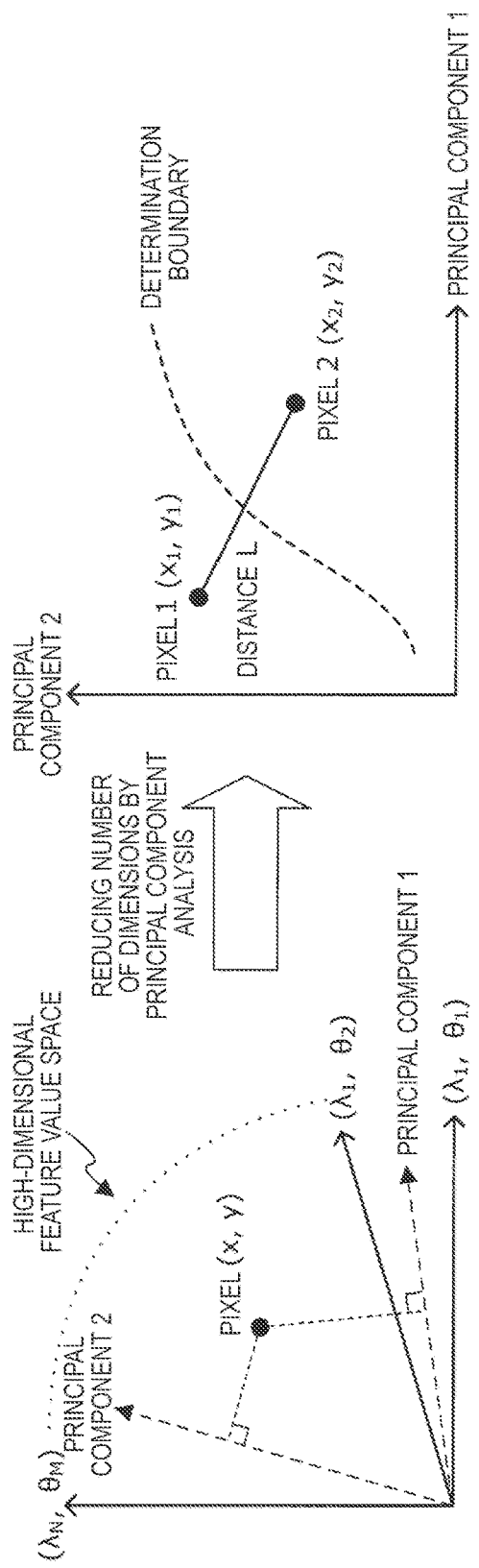
FIG. 12D is an explanatory diagram for describing a conversion process of a feature value and an indexing process of a surface property according to the embodiment.

Also, the surface property indexing unit 225 may perform the above indexing process and determination process, by utilizing the feature value (the second feature value) whose dimension is compressed by the feature value converting unit 223, as schematically illustrated in FIG. 12D, for example.

Further, the surface property indexing unit 225 may secondarily calculate a new feature value by utilizing the brightness value that composes the processing target image, to index the surface property of the measured object and determine the surface property by utilizing the calculated secondary feature value. This secondary feature value is not limited particularly, but a publicly known feature value that can be calculated by utilizing the brightness value can be utilized.

The above secondary feature value is, for example, a variation degree (for example, a statistics amount such as a variance value) of the brightness value of the pixel that is positioned around the pixel position of interest, which includes the brightness value at the pixel position of interest. For example, as schematically illustrated in FIG. 13, a rectangular region including p pixels×q pixels centered at a pixel P may be set with respect to the pixel P of interest in the processing target image, to calculate the variance value of the brightness value of the pixel P in the rectangular region and to set the variance value as the above secondary feature value. Here, the size of the rectangular region of interest is not limited particularly, but may be a square region of 5 pixels×5 pixels as illustrated in FIG. 13, and may be a rectangular region in which p is not equal to q.

Also, the above secondary feature value is, for example, a gradient of the brightness value of the pixel that is positioned around the pixel position of interest, which includes the brightness value at the pixel position of interest. For example, as schematically illustrated in FIG. 13, directions such as 0° direction, 45° direction, 90° direction, . . . , 275° direction with the pixel P at the center are considered with respect to the pixel P of interest in the processing target image. With regard to these directions, how much the brightness value of the surrounding pixel changes is calculated and set as the magnitude of the gradient. A numerical value group of the gradient obtained as described above (this numerical value group includes vector amounts that are associated with the direction and the magnitude of the gradient) may be set as the above secondary feature value.

As described above, the surface property indexing unit 225 according to the present embodiment indexes the surface property of the measured object, by integratively processing the feature values, by utilizing the feature values extracted from the processing target images based on the wavelengths and the reflection angles of various reflected lights, which are schematically illustrated in FIG. 9.

The surface property indexing unit 225 outputs the indexing result and the determination result obtained as described above, to the result output unit 227 described later.

For example, the result output unit 227 is configured with a CPU, a ROM, and a RAM. The result output unit 227 outputs, to the display control unit 207, information relevant to the indexing result and the determination result of the surface property of the measured object which is output from the surface property indexing unit 225. Thereby, the information relevant to the surface property of the metal strip S of the measured object is output to a display unit (not depicted). Also, the result output unit 227 may output the obtained indexing result and the determination result to an external device such as a process computer system for production management, and may create various types of record files relevant to products by utilizing the obtained indexing result. Also, the result output unit 227 may contain information relevant to the indexing result and the determination result of the surface property, as history information, in the storage unit 209 or the like, in association with time point information relevant to date and time at which the information is calculated.

In the above, an example of the function of the arithmetic processing apparatus 200 according to the present embodiment has been illustrated. Each of the above components may be configured with a general-purpose member or circuit, and may be configured with hardware specialized for the function of each component. Also, a CPU or the like may perform all of the functions of respective components. Thus, a utilized configuration can be changed as appropriate, according to the technology level at the time of performing the present embodiment.

Note that the computer program for providing each function of the arithmetic processing apparatus according to the above present embodiment can be created and implemented in a personal computer or the like. Also, a computer-readable recording medium that contains this computer program can be provided as well. For example, the recording medium is a magnetic disk, an optical disc, a magneto-optical disk, a flash memory, or the like. Also, the above computer program may be delivered via a network for example, without using the recording medium.

In the above, the surface property indexing apparatus according to the present embodiment has been described in detail, with reference to FIGS. 1 to 13.

(With Regard to Surface Property Indexing Method)

Figure 14:
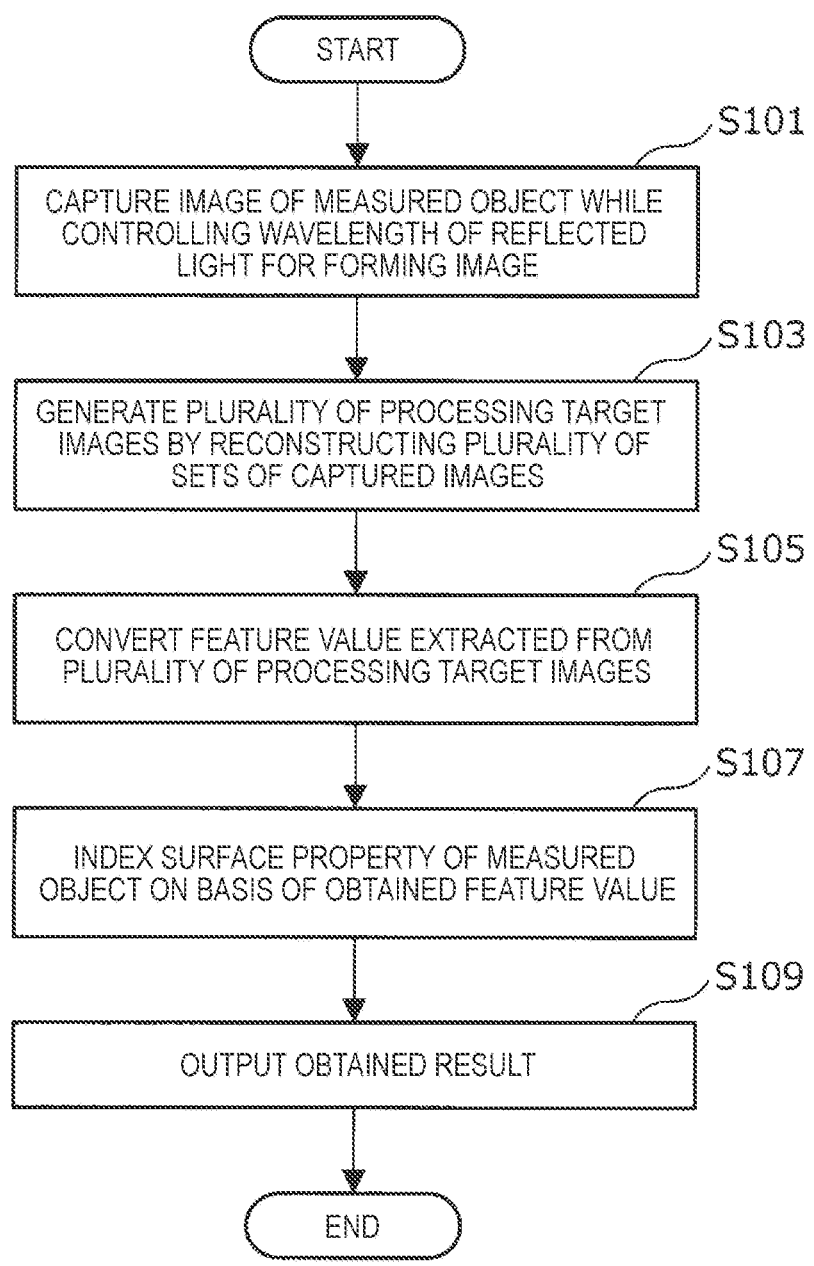
FIG. 14 is a flow diagram illustrating an example of a sequence of a surface property indexing method according to the embodiment.

Next, with reference to FIG. 14, an example of a sequence of a surface property indexing method according to the present embodiment will be described simply. FIG. 14 is a flow diagram illustrating an example of the sequence of the surface property indexing method according to the present embodiment.

First, the measurement device 100 of the surface property indexing apparatus 10 captures an image of a predetermined region of the surface of the metal strip S of the measured object, while controlling the wavelength of the reflected light that forms an image in the image capturing device, under the control of the measurement control unit 203 of the arithmetic processing apparatus 200 (step S101), to generate a plurality of captured images corresponding to a plurality of different wavelengths respectively with respect to the same view field of the surface of the metal strip S, and to sequentially generate a plurality of sets of a plurality of captured images while shifting the view field. Thereafter, the measurement device 100 outputs the generated sets of captured images to the arithmetic processing apparatus 200.

Upon acquiring a plurality of sets of brightness data composed of a plurality of captured images of the same view field which are output from the measurement device 100, the data acquiring unit 201 of the arithmetic processing apparatus 200 outputs the acquired brightness data to the image reconstructing unit 221 of the data processing unit 205.

The image reconstructing unit 221 of the arithmetic processing apparatus 200 generates a plurality of processing target images by reconstructing a plurality of sets of captured images generated by the measurement device 100, by the method described above (step S103). Thereafter, the image reconstructing unit 221 outputs the generated processing target images to the feature value converting unit 223 and the surface property indexing unit 225.

The feature value converting unit 223 of the arithmetic processing apparatus 200 converts the feature value extracted from the processing target images as necessary (step S105), and compresses the dimension of the feature value extracted from the processing target images. When performing the conversion process of the feature value, the feature value converting unit 223 outputs information relevant to the feature value after conversion to the surface property indexing unit 225.

The surface property indexing unit 225 of the arithmetic processing apparatus 200 indexes the surface property of the measured object on the basis of the obtained feature value (step S107). Also, the surface property indexing unit 225 may further determine the surface property, by utilizing the obtained indexing result. When a result of indexing is obtained, the surface property indexing unit 225 outputs the obtained result to the result output unit 227.

When the information of the surface property is output from the surface property indexing unit 225, the result output unit 227 outputs the obtained result to a user and various types of devices provided outside (step S109). Thereby, the user can recognize the result of the surface property of the metal strip S of the measured object.

In the above, with reference to FIG. 14, an example of the surface property indexing method performed by the surface property indexing apparatus 10 according to the present embodiment has been described simply.

(Hardware Configuration)

Figure 15:
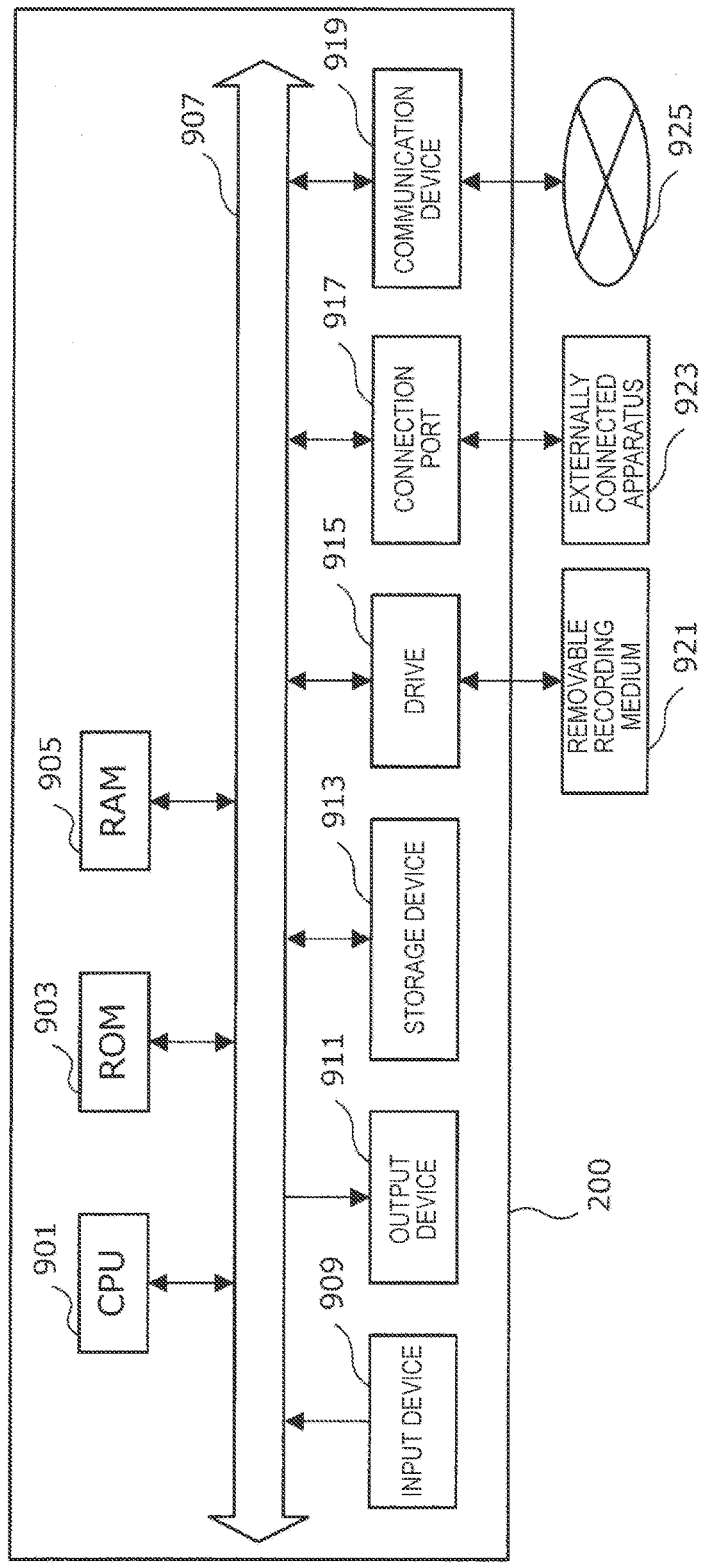
FIG. 15 is a block diagram illustrating an example of a hardware configuration of an arithmetic processing apparatus according to an embodiment of the present invention.

Next, the hardware configuration of the arithmetic processing apparatus 200 according to the embodiment of the present invention will be described in detail with reference to FIG. 15. FIG. 15 is a block diagram for illustrating the hardware configuration of the arithmetic processing apparatus 200 according to the embodiment of the present disclosure.

The arithmetic processing apparatus 200 mainly includes a CPU 901, a ROM 903, and a RAM 905. Furthermore, the arithmetic processing apparatus 200 also includes a bus 907, an input device 909, an output device 911, a storage device 913, a drive 915, a connection port 917, and a communication device 919.

The CPU 901 serves as an arithmetic processing apparatus and a control device, and controls the overall operation or a part of the operation of the arithmetic processing apparatus 200 according to various programs recorded in the ROM 903, the RAM 905, the storage device 913, or a removable recording medium 921. The ROM 903 stores programs, operation parameters, and the like used by the CPU 901. The RAM 905 primarily stores programs that the CPU 901 uses and parameters and the like varying as appropriate during the execution of the programs. These are connected with each other via the bus 907 configured from an internal bus such as a CPU bus or the like.

The bus 907 is connected to the external bus such as a PCI (Peripheral Component Interconnect/Interface) bus via the bridge.

The input device 909 is an operation means operated by a user, such as a mouse, a keyboard, a touch panel, buttons, a switch and a lever. Also, the input device 909 may be a remote control means (a so-called remote control) using, for example, infrared light or other radio waves, or may be an externally connected apparatus 923 such as a PDA conforming to the operation of the arithmetic processing apparatus 200. Furthermore, the input device 909 generates an input signal based on, for example, information which is input by a user with the above operation means, and is configured from an input control circuit for outputting the input signal to the CPU 901. The user of the surface property indexing apparatus 10 can input various data to the arithmetic processing apparatus 200 and can instruct the arithmetic processing apparatus 200 to perform processing by operating this input apparatus 909.

The output device 911 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, a mobile phone, a facsimile machine, and the like. For example, the output device 911 outputs a result obtained by various processings performed by the arithmetic processing apparatus 200. More specifically, the display device displays, in the form of texts or images, a result obtained by various processes performed by the arithmetic processing apparatus 200. On the other hand, the audio output device converts an audio signal such as reproduced audio data and sound data into an analog signal, and outputs the analog signal.

The storage device 913 is a device for storing data configured as an example of a storage unit of the arithmetic processing apparatus 200 and is used to store data. The storage device 913 is configured from, for example, a magnetic storage device such as a HDD (Hard Disk Drive), a semiconductor storage device, an optical storage device, or a magneto-optical storage device. This storage device 913 stores programs to be executed by the CPU 901, various data, and various data obtained from the outside.

The drive 915 is a reader/writer for recording medium, and is embedded in the arithmetic processing apparatus 200 or attached externally thereto. The drive 915 reads information recorded in the attached removable recording medium 921 such as a magnetic disk, an optical disk, a magneto-optical disk, or a semiconductor memory, and outputs the read information to the RAM 905. Furthermore, the drive 915 can write in the attached removable recording medium 921 such as a magnetic disk, an optical disk, a magneto-optical disk, or a semiconductor memory. The removable recording medium 921 is, for example, a CD medium, a DVD medium, or a Blu-ray medium. The removable recording medium 921 may be a CompactFlash (CF; registered trademark), a flash memory, an SD memory card (Secure Digital Memory Card), or the like. Alternatively, the removable recording medium 921 may be, for example, an IC card (Integrated Circuit Card) equipped with a non-contact IC chip or an electronic appliance.

The connection port 917 is a port for allowing devices to directly connect to the arithmetic processing apparatus 200. Examples of the connection port 917 include a USB (Universal Serial Bus) port, an IEEE1394 port, a SCSI (Small Computer System Interface) port, an RS-232C port, and the like. By the externally connected apparatus 923 connecting to this connection port 917, the arithmetic processing apparatus 200 directly obtains various data from the externally connected apparatus 923 and provides various data to the externally connected apparatus 923.

The communication device 919 is a communication interface configured from, for example, a communication device for connecting to a communication network 925. The communication device 919 is, for example, a wired or wireless LAN (Local Area Network), Bluetooth (registered trademark), a communication card for WUSB (Wireless USB), or the like. Alternatively, the communication device 919 may be a router for optical communication, a router for ADSL (Asymmetric Digital Subscriber Line), a modem for various communications, or the like. This communication device 919 can transmit and receive signals and the like in accordance with a predetermined protocol such as TCP/IP on the Internet and with other communication devices, for example. The communication network 925 connected to the communication device 919 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the arithmetic processing apparatus 200 according to the embodiment of the present invention has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

The preferred embodiment(s) of the present invention has/have been described above with reference to the accompanying drawings, whilst the present invention is not limited to the above examples. A person skilled in the art may find various alterations and modifications within the scope of the appended claims, and it should be understood that they will naturally come under the technical scope of the present invention.

REFERENCE SIGNS LIST

10 surface property indexing apparatus
11 conveyance roll
13 encoder
100 measurement device
101 illumination light source
103 image capturing device (two-dimensional camera)
105 wavelength selection mechanism
200 arithmetic processing apparatus
201 data acquiring unit
203 measurement control unit
205 data processing unit
207 display control unit
209 storage unit
221 image reconstructing unit
223 feature value converting unit
225 surface property indexing unit
227 result output unit

The invention claimed is:

1. A surface property indexing apparatus comprising:
a measurement device, including an illumination light source and an image capturing device, configured to radiate an illumination light on a surface of a measured object, and capture an image of a reflected light of the illumination light on the surface of the measured object, while selecting a wavelength, to generate a plurality of captured images; and
an arithmetic processing apparatus, including circuitry, configured to index a surface property of the measured object on the basis of the plurality of captured images generated by the measurement device,
wherein the measurement device includes
the illumination light source configured to radiate the illumination light on the surface of the measured object,
the image capturing device configured to capture images of the reflected light from the surface of the measured object, and
a wavelength selection mechanism, including a filter, configured to select a wavelength of the reflected light that forms an image in the image capturing device,
wherein a wavelength switching timing in the wavelength selection mechanism and an image capturing timing in the image capturing device are synchronized with the movement of a measuring object in the longitudinal direction, and the captured images generated by the image capturing device are images of the same wavelength of the reflected light that forms the images in the image capturing device and of different reflection angles of the reflected light that forms the images in the image capturing device in a direction corresponding to a longitudinal direction of the measured object in the captured images,
wherein the measurement device generates a plurality of the captured images corresponding to a plurality of different wavelengths respectively with respect to a same view field of the measured object, and sequentially generates a plurality of sets of the plurality of captured images, while shifting the view field, and
wherein the arithmetic processing apparatus includes
a processor configured to perform reconstruction by utilizing the plurality of sets of the plurality of captured images, to generate plurality of processing target images, with respect to a same view field of the measured object, having a common wavelength of the reflected light and a common reflection angle of the reflected light and composed of pixels corresponding to different view field positions of the measured object, for each combination of a wavelength of the reflected light and a reflection angle of the reflected light, the processor further configured to index a surface property of the measured object on the basis of a plurality of the processing target images generated by the processor.

2. The surface property indexing apparatus according to claim 1, wherein
the arithmetic processing apparatus further includes a feature value converting unit that converts a feature value extracted from the plurality of processing target images,
the feature value converting unit converts the feature value in a first feature value space specified by the wavelength and the reflection angle of the reflected light, which is extracted from the plurality of processing target images, to a feature value in a second feature value space of a smaller number of dimensions than the first feature value space, and
the processor indexes the surface property of the measured object, by utilizing the feature value in the second feature value space.

3. The surface property indexing apparatus according to claim 2, wherein
the feature value converting unit performs principal component analysis to the feature value in the first feature value space, to compress the number of dimensions of the first feature value space to the number of dimensions of the second feature value space.

4. The surface property indexing apparatus according to claim 1, wherein the measurement device captures an image of the surface of the measured object, at a position where the surface of the measured object curves.

5. The surface property indexing apparatus according to claim 2, wherein
the measurement device captures an image of the surface of the measured object, at a position where the surface of the measured object curves.

6. The surface property indexing apparatus according to claim 3, wherein
the measurement device captures an image of the surface of the measured object, at a position where the surface of the measured object curves.

7. The surface property indexing apparatus according to claim 1, wherein
the wavelength selection mechanism is a liquid crystal tunable filter or an acoust-optic tunable filter.

8. The surface property indexing apparatus according to claim 2, wherein
the processor calculates, as a secondary feature value, by using a brightness value at a pixel position of interest that is the feature value extracted from the plurality of processing target images, at least one of a variation degree of brightness values of pixels that are positioned around the pixel position of interest, including the brightness value at the pixel position of interest, and a gradient of the brightness values of the pixels that are positioned around the pixel position of interest, including the brightness value at the pixel position of interest, and
the processor indexes the surface property of the measured object by using at least one of the brightness value at the pixel position of interest, the variation degree of brightness values of pixels that are positioned around the pixel position of interest, and the gradient of the brightness values of the pixels that are positioned around the pixel position of interest.

9. The surface property indexing apparatus according to claim 3, wherein
the processor calculates, as a secondary feature value, by using a brightness value at a pixel position of interest that is the feature value extracted from the plurality of processing target images, at least one of a variation degree of brightness values of pixels that are positioned around the pixel position of interest, including the brightness value at the pixel position of interest, and a gradient of the brightness values of the pixels that are positioned around the pixel position of interest, including the brightness value at the pixel position of interest, and
the processor indexes the surface property of the measured object by using at least one of the brightness value at the pixel position of interest, the variation degree of brightness values of pixels that are positioned around the pixel position of interest, and the gradient of the brightness values of the pixels that are positioned around the pixel position of interest.

10. The surface property indexing apparatus according to claim 1, wherein
the measured object is titanium or titanium alloy, a stainless steel plate, a color coated steel plate, a laminated steel plate, or a plated steel plate.

11. A surface property indexing method comprising:
a measurement step of measuring a surface of a measured object by a measurement device that radiates an illumination light on the surface of the measured object and captures an image of a reflected light of the illumination light on the surface of the measured object while selecting a wavelength of the reflected light that forms an image in an image capturing device, and generating a plurality of captured images of the same wavelength of the reflected light that forms the image in the image capturing device and of different reflection angles of the reflected light that forms the image in the image capturing device in a direction corresponding to a longitudinal direction of the measured object in the captured images, for a same view field of the measured object, corresponding to a plurality of different wavelengths respectively, and generating a plurality of sets of the plurality of captured images sequentially while shifting the view field, wherein a wavelength switching timing in a wavelength selection mechanism and an image capturing timing in the image capturing device are synchronized with the movement of the measuring object in the longitudinal direction;
an image reconstructing step of performing reconstruction by utilizing the plurality of sets of the plurality of captured images generated by the measurement device, by an arithmetic processing apparatus that indexes a surface property of the measured object, to generate plurality of processing target images, with respect to a same view field of the measured object, having a common wavelength of the reflected light and a common reflection angle of the reflected light and composed of pixels corresponding to different view field positions of the measured object, for each combination of a wavelength of the reflected light and a reflection angle of the reflected light; and
a surface property indexing step of indexing the surface property of the measured object on the basis of a plurality of the processing target images generated in the image reconstructing step, by the arithmetic processing apparatus.

12. The surface property indexing method according to claim 11, further comprising:
a feature value converting step of converting a feature value extracted from the plurality of processing target images, between the image reconstructing step and the surface property indexing step,
wherein, in the feature value converting step, the feature value in a first feature value space specified by the wavelength and the reflection angle of the reflected light, which is extracted from the plurality of processing target images, is converted to a feature value in a second feature value space of a smaller number of dimensions than the first feature value space, and
in the surface property indexing step, the surface property of the measured object is indexed, by utilizing the feature value in the second feature value space.

13. The surface property indexing method according to claim 12, wherein
in the feature value converting step, principal component analysis is performed to the feature value in the first feature value space, to compress the number of dimensions of the first feature value space to the number of dimensions of the second feature value space.

14. The surface property indexing method according to claim 11, wherein
the measurement device captures an image of the surface of the measured object at a position where the surface of the measured object curves.

15. The surface property indexing method according to claim 12, wherein the measurement device captures an image of the surface of the measured object at a position where the surface of the measured object curves.

16. The surface property indexing method according to claim 13, wherein
the measurement device captures an image of the surface of the measured object at a position where the surface of the measured object curves.

17. The surface property indexing method according to claim 12, wherein
in the surface property indexing step, calculating, as a secondary feature value, by using a brightness value at a pixel position of interest that is the feature value extracted from the plurality of processing target images, at least one of a variation degree of brightness values of pixels that are positioned around the pixel position of interest, including the brightness value at the pixel position of interest, and a gradient of the brightness values of the pixels that are positioned around the pixel position of interest, including the brightness value at the pixel position of interest, and
indexing the surface property of the measured object by using at least one of the brightness value at the pixel position of interest, the variation degree of brightness values of pixels that are positioned around the pixel position of interest, and the gradient of the brightness values of the pixels that are positioned around the pixel position of interest.

18. The surface property indexing method according to claim 13, wherein
in the surface property indexing step, calculating, as a secondary feature value, by using a brightness value at a pixel position of interest that is the feature value extracted from the plurality of processing target images, at least one of a variation degree of brightness values of pixels that are positioned around the pixel position of interest, including the brightness value at the pixel position of interest, and a gradient of the brightness values of the pixels that are positioned around the pixel position of interest, including the brightness value at the pixel position of interest, and
indexing the surface property of the measured object by using at least one of the brightness value at the pixel position of interest, the variation degree of brightness values of pixels that are positioned around the pixel position of interest, and the gradient of the brightness values of the pixels that are positioned around the pixel position of interest.

19. The surface property indexing method according to claim 11, wherein
the measured object is titanium or titanium alloy, a stainless steel plate, a color coated steel plate, a laminated steel plate, or a plated steel plate.

20. A recording medium having a program for causing a computer that is capable of communicating with each other with a measurement device that radiates an illumination light on a surface of a measured object, and captures an image of a reflected light of the illumination light on the surface of the measured object while selecting a wavelength of the reflected light that forms an image in an image capturing device, and thereby generates a plurality of captured images of the same wavelength of the reflected light that forms the image in the image capturing device and of different reflection angles of the reflected light that forms the image in the image capturing device in a direction corresponding to a longitudinal direction of the measured object in the captured images, for a same view field of the measured object, corresponding to a plurality of different wavelengths respectively, and sequentially generates a plurality of sets of the plurality of captured images while shifting the view field, to implement, wherein, a wavelength switching timing in a wavelength selection mechanism and an image capturing timing in the image capturing device are synchronized with a movement of the measuring object in the longitudinal direction:
an image reconstruction function of performing reconstruction by utilizing the plurality of sets of the plurality of captured images, to generate plurality of processing target images, with respect to a same view field of the measured object, having a common wavelength of the reflected light and a common reflection angle of the reflected light and composed of pixels corresponding to different view field positions of the measured object, for each combination of a wavelength of the reflected light and a reflection angle of the reflected light; and
a surface property indexing function of indexing a surface property of the measured object on the basis of a plurality of the processing target images generated by the image reconstruction function.

21. The recording medium according to claim 20, wherein
the program causes the computer to further implement a feature value conversion function of converting a feature value extracted from the plurality of processing target images,
the feature value conversion function converts the feature value in a first feature value space specified by the wavelength and the reflection angle of the reflected light, which is extracted from the plurality of processing target images, to a feature value in a second feature value space of a smaller number of dimensions than the first feature value space, and
the surface property indexing function indexes the surface property of the measured object, by utilizing the feature value in the second feature value space.

22. The recording medium according to claim 21, wherein
the feature value conversion function performs principal component analysis to the feature value in the first feature value space to compress the number of dimensions of the first feature value space to the number of dimensions of the second feature value space.

23. The recording medium according to claim 21, wherein
the surface property indexing function calculates, as a secondary feature value, by using a brightness value at a pixel position of interest that is the feature value extracted from the plurality of processing target images, at least one of a variation degree of brightness values of pixels that are positioned around the pixel position of interest, including the brightness value at the pixel position of interest, and a gradient of the brightness values of the pixels that are positioned around the pixel position of interest, including the brightness value at the pixel position of interest, and
the surface property indexing function indexes the surface property of the measured object by using at least one of the brightness value at the pixel position of interest, the variation degree of brightness values of pixels that are positioned around the pixel position of interest, and the gradient of the brightness values of the pixels that are positioned around the pixel position of interest.

24. The recording medium according to claim 22, wherein
the surface property indexing function calculates, as a secondary feature value, by using a brightness value at a pixel position of interest that is the feature value extracted from the plurality of processing target images, at least one of a variation degree of brightness values of pixels that are positioned around the pixel position of interest, including the brightness value at the pixel position of interest, and a gradient of the brightness values of the pixels that are positioned around the pixel position of interest, including the brightness value at the pixel position of interest, and the surface property indexing function indexes the surface property of the measured object by using at least one of the brightness value at the pixel position of interest, the variation degree of brightness values of pixels that are positioned around the pixel position of interest, and the gradient of the brightness values of the pixels that are positioned around the pixel position of interest.

* * * * *